(12) United States Patent
Kaplan

(10) Patent No.: US 8,356,399 B2
(45) Date of Patent: Jan. 22, 2013

(54) METHOD FOR PROTECTING A RESONATING SENSOR

(75) Inventor: Shay Kaplan, Givat Elah (IL)

(73) Assignee: Microtech Medical Technologies Ltd., Tel Aviv (IL)

( * ) Notice: Subject to any disclaimer, the term of this patent is extended or adjusted under 35 U.S.C. 154(b) by 720 days.

(21) Appl. No.: 11/941,992

(22) Filed: Nov. 19, 2007

(65) Prior Publication Data

US 2008/0066550 A1   Mar. 20, 2008

Related U.S. Application Data

(62) Division of application No. 10/876,781, filed on Jun. 28, 2004, now Pat. No. 8,162,839.

(60) Provisional application No. 60/497,925, filed on Aug. 27, 2003.

(51) Int. Cl.
*H04R 31/00* (2006.01)

(52) U.S. Cl. ......... 29/594; 29/609.1; 181/171; 181/172; 310/321; 310/328; 310/330; 310/331; 310/333; 333/150; 333/187; 333/193; 333/195; 381/396; 381/398; 73/627; 73/649; 600/438; 600/459; 600/472

(58) Field of Classification Search .............. 29/592.1, 29/594, 609.1; 181/171, 172; 310/321, 328, 310/330–333; 381/396, 398; 333/150, 187, 333/193–196

See application file for complete search history.

(56) References Cited

U.S. PATENT DOCUMENTS

| | | |
|---|---|---|
| 3,640,271 A | 2/1972 | Horton |
| 3,742,937 A | 7/1973 | Manuel et al. |
| 3,853,117 A | 12/1974 | Murr |
| 3,946,724 A | 3/1976 | La Balme |
| 4,014,319 A | 3/1977 | Favre |
| 4,206,762 A | 6/1980 | Cosman |
| 4,237,454 A | 12/1980 | Meyer |
| 4,364,016 A * | 12/1982 | Tanski ............................ 333/193 |
| 4,442,574 A * | 4/1984 | Wanuga et al. ............... 29/25.35 |
| 4,686,764 A | 8/1987 | Adams |

(Continued)

FOREIGN PATENT DOCUMENTS

| | | |
|---|---|---|
| JP | 1-119729 A | 5/1989 |
| JP | 2-503828 T | 11/1990 |

(Continued)

OTHER PUBLICATIONS

Search Report of corresponding JP Application No. 2006-524526 dated Apr. 13, 2010.

(Continued)

*Primary Examiner* — Paul D Kim

(74) *Attorney, Agent, or Firm* — Cadwalader Wickersham & Taft LLP

(57) ABSTRACT

A method of protecting a resonating sensor is described. The protected resonating sensor may include at least one passive ultrasonically excitable resonating sensor unit. Each sensor unit has one or more vibratable members having a resonating frequency that varies as a function of a physical variable in a measurement environment. The sensor is protected by forming one or more protective chambers defined between a compliant member and the vibratable member(s). A substantially non-compressible medium is disposed within the protective chamber(s). The compliant member has a first side that may be exposed to a measurement environment and a second side that may be exposed to the substantially non-compressible medium. The substantially non-compressible medium may be a liquid or gel and is in contact with the vibratable member(s). When the medium is a liquid, the chamber is sealed. When the medium is a gel, the chamber may be sealed or non-sealed.

49 Claims, 7 Drawing Sheets

U.S. PATENT DOCUMENTS

| | | | |
|---|---|---|---|
| 4,733,561 | A | 3/1988 | Gilby |
| 4,867,169 | A | 9/1989 | Machida |
| 4,884,450 | A | 12/1989 | Greenwood et al. |
| 4,949,581 | A | 8/1990 | Rud, Jr. |
| 5,067,491 | A | 11/1991 | Taylor et al. |
| 5,212,988 | A | 5/1993 | White et al. |
| 5,260,762 | A | 11/1993 | Telle |
| 5,283,768 | A | 2/1994 | Rorden |
| 5,317,917 | A | 6/1994 | Dufor |
| 5,480,747 | A * | 1/1996 | Vasudev .................. 430/5 |
| 5,524,636 | A | 6/1996 | Sarvazyan et al. |
| 5,557,971 | A | 9/1996 | Uemura et al. |
| 5,619,997 | A | 4/1997 | Kaplan |
| 5,625,151 | A | 4/1997 | Yamaguchi |
| 5,666,706 | A * | 9/1997 | Tomita et al. ............. 29/25.35 |
| 5,749,364 | A | 5/1998 | Sliwa et al. |
| 5,833,603 | A * | 11/1998 | Kovacs et al. ............. 600/317 |
| 5,989,190 | A | 11/1999 | Kaplan |
| 5,997,477 | A | 12/1999 | Sehgal |
| 6,027,449 | A | 2/2000 | Mazess et al. |
| 6,083,165 | A | 7/2000 | Kaplan |
| 6,121,718 | A | 9/2000 | Mohr, III |
| 6,132,378 | A | 10/2000 | Marino |
| 6,142,954 | A | 11/2000 | Anhauser et al. |
| 6,163,026 | A * | 12/2000 | Bawolek et al. ............. 250/351 |
| 6,301,968 | B1 | 10/2001 | Maruyama et al. |
| 6,305,226 | B1 | 10/2001 | Barber et al. |
| 6,312,380 | B1 | 11/2001 | Hoek et al. |
| 6,331,163 | B1 | 12/2001 | Kaplan |
| 6,368,275 | B1 | 4/2002 | Sliwa et al. |
| 6,401,545 | B1 | 6/2002 | Monk |
| 6,461,301 | B2 | 10/2002 | Smith |
| 6,470,753 | B2 | 10/2002 | Maruyama |
| 6,550,337 | B1 | 4/2003 | Wagner et al. |
| 6,558,330 | B1 | 5/2003 | Ayter et al. |
| 6,770,032 | B2 | 8/2004 | Kaplan |
| 6,787,051 | B2 | 9/2004 | Silverbrook |
| 6,970,742 | B2 | 11/2005 | Mann |
| 7,134,341 | B2 | 11/2006 | Girmonsky et al. |
| 7,178,378 | B2 | 2/2007 | Crawley et al. |
| 7,415,883 | B2 | 8/2008 | Kaplan |
| 2005/0049499 | A1 | 3/2005 | Kaplan |
| 2005/0148205 | A1 | 7/2005 | Franosch et al. |

FOREIGN PATENT DOCUMENTS

| | | |
|---|---|---|
| JP | 9-508469 T | 8/1997 |
| JP | 2000-506410 T | 5/2000 |
| JP | 2001-061790 A | 3/2001 |
| WO | WO 89/08244 A1 | 9/1989 |
| WO | WO 95/20769 A1 | 8/1995 |
| WO | WO 97/33513 A1 | 9/1997 |
| WO | WO 2004/096007 A2 | 11/2004 |
| WO | WO 2005/022110 A3 | 3/2005 |
| WO | WO 2006/001017 A2 | 1/2006 |

OTHER PUBLICATIONS

Supplemental European Search Report of corresponding EP Application No. 04745064.8-2305 dated Sep. 14, 2006.

Office Actions and Responses of related U.S. Appl. No. 10/876,781: Non-Final Rejection dated Sep. 14, 2010; Amendment and Response to Final Rejection with Request for Continued Examination and two-month Extension of Time dated Aug. 23, 2010; Final Rejection dated Mar. 25, 2010; Amendment and Response to Non-Final Rejection with three-month Extension of Time dated Jan. 13, 2010; Non-Final Rejection dated Jul. 17, 2009; Amendment and Response to Non-Final Rejection with three-month Extension of Time dated Jul. 6, 2008; Non-Final Rejection dated Jan. 4, 2008; Response to Requirement for Restriction/Election with two-month Extension of Time dated Sep. 24, 2007; and Requirement for Restriction/Election dated Jul. 2, 2007.

U.S. Appl. No. 09/004,420, filed Jan. 8, 1998, Richter.

European Search Report from corresponding EP 11151737.1-2310 dated Apr. 12, 2011, 7 pages.

* cited by examiner

METHOD FOR PROTECTING A RESONATING SENSOR

CROSS-REFERENCE TO RELATED APPLICATIONS

This application is a divisional application claiming benefit from U.S. patent application Ser. No. 10/876,781 filed Jun. 28, 2004, now U.S. Pat. No. 8,162,839 which claims priority from U.S. Provisional Patent Application No. 60/497,925, filed Aug. 27, 2003, both of which are incorporated herein by reference in their entirety.

FIELD OF THE INVENTION

The present invention relates generally to the field of resonating sensors in general and to a method for protecting resonating sensors from deposition of extraneous materials or tissues and protected resonating sensors in particular.

BACKGROUND OF THE INVENTION

Methods, devices and systems, using resonating sensors for determining the values of various physical parameters in a measurement environment are well known in the art. For example, methods systems and devices for using ultrasonically activated passive sensors for sensing and measuring the values of different physical parameters within a human body or in other environments and scientific and industrial applications, have been described. U.S. Pat. No. 5,619,997 to Kaplan, incorporated herein by reference in its entirety for all purposes, discloses a passive sensor system using ultrasonic energy.

An ultrasonic activation and detection system ultrasonically activates passive sensors having vibratable parts (such as vibratable beams or vibratable membranes) which sensor(s) may be implanted in a body or disposed in other environments, by directing a beam of ultrasound at the passive sensor or sensors. The activated passive sensor(s), or vibratable parts thereof, vibrate or resonate at a frequency that is a function of the value of the physical variable to be measured. The passive sensors thus absorb ultrasonic energy from the exciting ultrasonic beam at the frequency (or frequencies) of the exciting ultrasonic beam. The amplitude of vibration of a vibratable part of such a passive sensor is maximal when the frequency of the exciting ultrasonic beam is identical to the resonance frequency of the vibratable sensor part (such as, for example a vibratable membrane or a vibratable beam included in the passive sensor). The frequency (or frequencies) at which the passive sensor absorbs and/or emits energy may be detected by a suitable detector and used to determine the value of the physical parameter.

The physical parameters measurable with such passive ultrasonic sensors may include, but are not limited to, temperature, pressure, a concentration of a chemical species in the fluid or medium in which the sensor is immersed or disposed, and the like.

If the exciting ultrasonic beam is pulsed, the ultrasonic sensor may continue to vibrate after the excitation beam is turned off. The ultrasonic radiation emitted by the activated passive sensor after turning the exciting ultrasonic beam off may be detected and used to determine the value of the physical parameter of interest.

Since more than one physical variable may influence the vibration frequency of passive sensors, a correction may be needed in order to compensate for the effects of other physical parameters unrelated to the physical parameter which needs to be determined on the measured sensor vibration frequency. For example, if pressure is the physical parameter to be determined, changes in temperature may affect the vibration frequency of the sensor. U.S. Pat. Nos. 5,989,190 and 6,083,165 to Kaplan, both patents are incorporated herein by reference in their entirety for all purposes, disclose compensated sensor pairs and methods for their use for compensating for the effects of unrelated different physical variables on the determined value of another physical variable which is being determined. For example, such compensated sensor pairs, may be used for compensating for inaccuracies in pressure measurements due to temperature changes.

U.S. Pat. No. 6,331,163 to Kaplan, incorporated herein by reference in its entirety for all purposes, discloses implantable passive sensors having a protective coating, and various types of sensor positioners or sensor anchoring devices. Such sensors may be used, inter alia, for measuring intraluminal blood pressure by intraluminal implantation of the sensor(s).

Co-pending U.S. patent application Ser. No. 10/828,218 to Girmonsky et al. entitled "METHODS AND DEVICES FOR DETER G THE RESONANCE FREQUENCY OF PASSIVE MECHANICAL RESONATORS" filed on Apr. 21, 2004 incorporated herein by reference in its entirety for all purposes, discloses, inter alia, methods, resonating sensors and systems, that use a Doppler shift based method for determining the resonance frequency of passive resonators. The methods, sensors and systems, may be applied, inter alia, for sensing pressure or other physical parameters in a measurement environment, such as, but not limited to, the in-vivo measurement of blood pressure within a part of a cardiovascular system.

While all the above examples are related to passive resonating ultrasonic sensors, many other types of resonating sensors including both active and passive sensors are known in the art for measurement of various different physical parameters. Such sensors have in common the use of one or more resonating vibratable structures or parts, such as, for example vibratable membranes or beams or the like, which may be passively or actively vibrated. The resonance frequency of the resonating structure of such sensors changes as a function of the physical variable to be determined and may be sensed or measured in various different ways and used to determine the value of the physical variable. Examples of such sensors are the active ultrasonic sensor disclosed in U.S. Pat. No. 6,461,301 to Smith. Additional sensor types are disclosed in U.S. Pat. No. 6,312,380 to Hoek et al.

A common problem when resonating sensors such as, but not limited to, the sensors described above are implanted within a living body is the deposition of tissue or other materials of biological origin on the sensor or on parts thereof. For example, various substances or living cells may attach to the surface of the resonating sensor or to various parts thereof and adjacent tissues may cause the deposition of a layer or film of material and/or cells, and/or tissues on the sensor's surface. The deposition of tissues or other biological materials on the vibratable part of the sensor, such as (but not limited to) the vibratable membrane of a passive (or active) resonating sensor may cause changes in the vibratable membrane (or the other vibratable part) resonance characteristics such as, inter alia, the resonance frequency, sensitivity to stress, and vibration amplitude of the vibratable membrane. Such changes may adversely affect the sensor's performance and the accuracy of the determination of the physical variable which is to be determined.

Similarly, when a resonating sensor is disposed within a fluid or gas or other medium or measurement environment which contains various substances (such as, for example, within a chemical reaction mixture in a reactor or in a measurement environment containing sprays or aerosols or the like), deposition of liquid or solid material or particles on the vibratable part of the resonating sensor may similarly affect the resonance characteristics of the vibratable part of the sensor with similar adverse effects on the sensor's performance.

BRIEF DESCRIPTION OF THE DRAWINGS

The invention is herein described, by way of example only, with reference to the accompanying drawings, in which like components are designated by like reference numerals, wherein.

SUMMARY OF THE INVENTION

Figure 1:
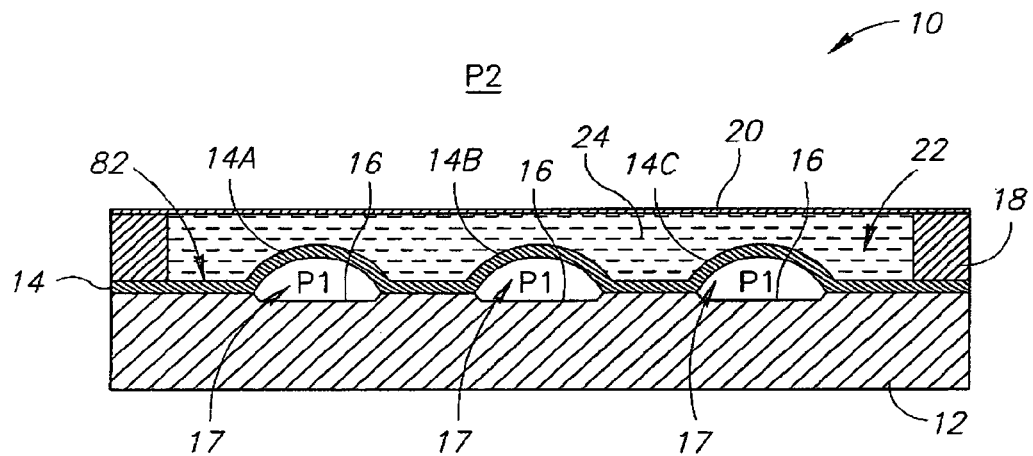
FIG. 1 is a schematic cross-sectional view illustrating a protected passive ultrasonic pressure sensor having multiple vibratable membranes, in accordance with an embodiment of the present invention.

There is therefore provided, in accordance with an embodiment of the present invention, a protected resonating sensor. The sensor includes at least one resonating sensor unit. Each sensor unit of the resonating sensor units has at least one vibratable member. The sensor also includes a compliant member. The compliant member forms part of at least one chamber. The compliant member has a first side and a second side. The first side is configured to be exposed to a first medium in a measurement environment. The sensor further includes a substantially non-compressible medium disposed within the at least one chamber. The substantially non-compressible medium is in contact with the at least one vibratable member of the at least one resonating sensor unit and with the second side of the compliant member.

In accordance with an aspect of the invention, the protected sensor is configured for protecting the at least one vibratable member from the deposition of extraneous material thereupon.

Furthermore, in accordance with an embodiment of the present invention, the medium is a substantially non-compressible liquid and the at least one chamber is a sealed chamber.

Furthermore, in accordance with an embodiment of the present invention, the medium is a substantially non-compressible gel and the at least one chamber is selected from a sealed chamber and a non-sealed chamber.

Furthermore, in accordance with an embodiment of the present invention, the protected resonating sensor is attached to a supporting device.

Furthermore, in accordance with an embodiment of the present invention, the supporting device is selected from a sensor anchor, a sensor positioner, an implantable graft, a sensor fixating device, an implant, an implantable device, part of an implantable device, a pacemaker, part of a pacemaker, a defibrillator, part of a defibrillator, an implantable electrode, an insertable electrode, an endoscopic device, part of an endoscopic device, an autonomous endoscopic device, a part of an autonomous endoscopic device, a tethered endoscopic device, a part of a tethered endoscopic device, an implantable catheter, an insertable catheter, a stent, a part of a stent, a guide-wire, a part of a guide-wire, an implantable therapeutic substance releasing device, and an insertable therapeutic substance releasing device.

Furthermore, in accordance with an embodiment of the present invention, the substantially non-compressible medium completely fills the at least one chamber.

Furthermore, in accordance with an embodiment of the present invention, the substantially non-compressible medium is selected from a substantially non-compressible liquid and a substantially non-compressible gel.

Furthermore, in accordance with an embodiment of the present invention, the protected sensor is an implantable protected sensor configured for implantation within an organism and the acoustic impedance of the compliant member is close to or equal to the acoustic impedance of at least one tissue or bodily fluid of the organism.

Furthermore, in accordance with an embodiment of the present invention, the protected sensor includes a housing attached to the compliant member to form at least one chamber.

Furthermore, in accordance with an embodiment of the present invention, the at least one chamber comprises at least one sealed chamber and the housing is sealingly attached to the compliant member to form the at least one sealed chamber.

Furthermore, in accordance with an embodiment of the present invention, the protected sensor includes at least one spacer member sealingly attached to the at least one resonating sensor unit and to the compliant member to form the at least one sealed chamber.

Furthermore, in accordance with an embodiment of the present invention, the at least one spacer member is attached to the at least one resonating sensor unit and to the compliant member to form the at least one chamber.

Furthermore, in accordance with an embodiment of the present invention, the at least one chamber comprises at least one sealed chamber and the at least one spacer member is sealingly attached to the at least one resonating sensor unit and to the compliant member to form the at least one sealed chamber.

Furthermore, in accordance with an embodiment of the present invention, the at least one chamber is selected from at least one chamber formed within a sensor anchoring device, and at least one chamber comprising part of a sensor anchoring device.

Furthermore, in accordance with an embodiment of the present invention, the sensor anchoring device is selected from a sensor anchor, a sensor positioner, an implantable graft, a sensor fixating device, an implant, an implantable device, an implantable graft, a part of an implantable device, a pacemaker, a part of a pacemaker, a defibrillator, a part of a defibrillator, an implantable electrode, an insertable electrode, an endoscopic device, a part of an endoscopic device, an autonomous endoscopic device, a part of an autonomous endoscopic device, a tethered endoscopic device, a part of a tethered endoscopic device, an implantable catheter, an insertable catheter, a stent, a part of a stent, a guide-wire, a part of a guide-wire, an implantable therapeutic substance releasing device, and an insertable therapeutic substance releasing device.

Furthermore, in accordance with an embodiment of the present invention, the at least one resonating sensor unit is selected from a passive resonating sensor unit and an active resonating sensor unit.

Furthermore, in accordance with an embodiment of the present invention, the at least one resonating sensor unit is selected from a passive ultrasonic resonating sensor unit and an active ultrasonic resonating sensor unit.

Furthermore, in accordance with an embodiment of the present invention, the at least one resonating sensor unit includes a substrate having one or more recesses formed therein and a second layer sealingly attached to the substrate to form one or more sealed sensor unit chambers within the resonating sensor unit.

Furthermore, in accordance with an embodiment of the present invention, the at least one vibratable member of the resonating sensor unit is selected from at least one vibratable member comprising a portion of the substrate, and at least one vibratable member comprising a portion of the second layer overlying one or more of the recesses.

Furthermore, in accordance with an embodiment of the present invention, each sealed sensor unit chamber of the one or more sealed sensor unit chambers has a pressure level therewithin.

Furthermore, in accordance with an embodiment of the present invention, the pressure level is selected from a zero pressure level and a non-zero pressure level.

Furthermore, in accordance with an embodiment of the present invention, the protected sensor includes a first resonating sensor unit having one or more sealed sensor unit chambers and at least a second resonating sensor unit having one or more sealed sensor unit chambers. The pressure level within at least one sealed sensor unit chamber of the first resonating sensor unit is different than the pressure level within at least one sealed sensor unit chamber of the at least second resonating sensor unit.

Furthermore, in accordance with an embodiment of the present invention, the at least one resonating sensor unit is selected from at least one passive ultrasonic pressure sensor having a single vibratable membrane, and at least one passive ultrasonic pressure sensor having multiple vibratable membranes.

Furthermore, in accordance with an embodiment of the present invention, the protected sensor is an implantable protected sensor and one or more of the components of the implantable protected sensor includes one or more materials selected from biocompatible materials and hemocompatible materials.

Furthermore, in accordance with an embodiment of the present invention, the protected sensor is configured for implantation within a measurement environment selected from, an eye, a urether, a cardiac chamber, a cardiovascular system, a part of a cardiovascular system, an annurismal sac after endovascular repair, a spine, an intervertebral disc, a spinal cord, a spinal column, an intracranial compartment, an intraluminal space of a blood vessel, an artery, a vein, an aorta, a pulmonary blood vessel, a carotid blood vessel, a brain blood vessel, and a coronary artery, a femoral artery, an iliac artery, a hepatic artery and a vena cava.

There is also provided a method for providing a protected resonating sensor. The method includes the step of enclosing one or more resonating sensor units in at least one chamber having at least one compliant member. Each sensor unit of the one or more resonating sensor units has at least one resonating part. The at least one chamber is filled with a substantially non-compressible medium. The at least one compliant member forms at least part of the walls of the at least one chamber. The at least one compliant member and the at least one resonating part are in contact with the substantially non-compressible medium.

Furthermore, in accordance with an embodiment of the present invention, the at least one compliant member comprises a compliant material selected from a polymer based material, a plastic material, Kapton®, a polyurethane based polymer, an ethylvinyl acetate based polymer, Echothane® CPC-41, Echothane® CPC-29, Echothane®, and a Parylene® based polymer.

Furthermore, in accordance with an embodiment of the present invention, the substantially non-compressible medium is a medium having a low vapor pressure.

Furthermore, in accordance with an embodiment of the present invention, the medium is a liquid and the step of enclosing includes sealingly enclosing one or more resonating sensor units in the at least one chamber to form at least one sealed chamber.

Furthermore, in accordance with an embodiment of the present invention, the substantially non-compressible medium is a gel selected from the group consisting of a synthetic gel, a natural gel, a hydrogel, a lipogel, a hydrophobic gel, a hydrophilic gel, a biocompatible gel, a hemocompatible gel, a polymer based gel, a cross-linked polymer based gel and combinations thereof.

Furthermore, in accordance with an embodiment of the present invention, the acoustic impedance of the substantially non-compressible medium is close to or equal to the acoustic impedance of a medium contained in a measurement environment in which said protected sensor is disposed.

Furthermore, in accordance with an embodiment of the present invention, the protected sensor is an implantable protected sensor configured for implantation within an organism and the acoustic impedance of the substantially non-compressible medium is close to or equal to the acoustic impedance of at least one tissue or bodily fluid of the organism.

Furthermore, in accordance with an embodiment of the present invention, the acoustic impedance of the compliant member is close to or equal to the acoustic impedance of a medium contained in a measurement environment in which the protected sensor is disposed.

Furthermore, in accordance with an embodiment of the present invention, the protected sensor is an implantable protected sensor configured for implantation within an organism and the acoustic impedance of the compliant member is close to or equal to the acoustic impedance of at least one tissue or bodily fluid of the organism.

Furthermore, in accordance with an embodiment of the present invention, the one or more resonating sensor units are selected from, a passive resonating sensor unit, an active resonating sensor unit, a passive ultrasonic resonating sensor unit, an active ultrasonic resonating sensor unit, a pressure sensor unit, a temperature sensor unit, a sensor for sensing the concentration of a chemical species in a measurement environment, and combinations thereof.

Furthermore, in accordance with an embodiment of the present invention, the step of enclosing includes disposing the one or more resonating sensor units in a housing, filling the housing with the substantially non-compressible medium, and attaching the at least one compliant member to the housing to form the at least one chamber.

Furthermore, in accordance with an embodiment of the present invention, the at least one chamber is a sealed chamber and the step of attaching includes sealingly attaching the at least one compliant member to the housing to form the at least one sealed chamber.

Furthermore, in accordance with an embodiment of the present invention, the step of disposing includes attaching the one or more resonating sensor units to the housing.

Furthermore, in accordance with an embodiment of the present invention the step of enclosing includes disposing the one or more resonating sensor units in a housing, attaching the at least one compliant member to the housing to form the at least one chamber, and filling the at least one chamber with the substantially non-compressible medium.

Furthermore, in accordance with an embodiment of the present invention, the step of enclosing further includes the step of sealing the at least one chamber to form at least one sealed chamber.

Furthermore, in accordance with an embodiment of the present invention, the step of disposing includes attaching the one or more resonating sensor units to the housing.

Furthermore, in accordance with an embodiment of the present invention, the step of filling includes filling the at least one chamber with the substantially non-compressible medium through at least one opening formed in the walls of the at least one chamber.

Furthermore, in accordance with an embodiment of the present invention, the at least one opening includes at least one opening formed in the housing.

Furthermore, in accordance with an embodiment of the present invention, the step of enclosing includes attaching at least one spacer member to the one or more resonating sensor units, attaching the at least one compliant member to the at least one spacer member to form the at least one chamber and filling the at least one chamber with the substantially non-compressible medium.

Furthermore, in accordance with an embodiment of the present invention, the first step of attaching, the second step of attaching and the step of filling are performed in the recited order and the method further includes the step of sealing the at least one chamber to form at least one sealed chamber.

Furthermore, in accordance with an embodiment of the present invention, the second step of attaching is performed after the step of filling and the second step of attaching includes attaching the at least one compliant member to the at least one spacer member to form said at least one chamber.

Furthermore, in accordance with an embodiment of the present invention, the second step of attaching includes sealingly attaching the at least one compliant member to the at least one spacer member to form at least one sealed chamber.

Furthermore, in accordance with an embodiment of the present invention, the second step of attaching is performed after the step of filling and the attaching includes forming the at least one compliant member on the at least one spacer member and on the substantially non-compressible medium to form the at least one chamber.

Furthermore, in accordance with an embodiment of the present invention, the forming includes depositing the at least one compliant member on the at least one spacer member and on the substantially non-compressible medium using a chemical vapor deposition method to form the at least one chamber.

Furthermore, in accordance with an embodiment of the present invention, the at least one chamber is a sealed chamber and the second step of attaching includes sealingly forming the at least one compliant member on the at least one spacer member and on the substantially non-compressible medium to form the at least one sealed chamber.

Furthermore, in accordance with an embodiment of the present invention, the step of sealingly forming includes sealingly depositing the at least one compliant member on the at least one spacer member and on the substantially non-compressible medium using a chemical vapor deposition method to form the at least one sealed chamber.

Furthermore, in accordance with an embodiment of the present invention, the step of filling occurs after the second step of attaching, and the filling of the at least one chamber with the substantially non-compressible medium is performed through at least one opening in the walls of the at least on chamber.

Furthermore, in accordance with an embodiment of the present invention, the method further includes the step of sealing the at least one opening in the walls of the at least one chamber after the step of filling.

Furthermore, in accordance with an embodiment of the present invention, the step of filling includes the steps of, forming a vacuum within the at least one chamber, disposing the protected sensor in the liquid to cover the at least one opening with the liquid, and allowing the liquid to fill the at least one chamber.

Furthermore, in accordance with an embodiment of the present invention, the substantially non-compressible medium is a gel, the liquid is a gel forming liquid and the method further includes the step of allowing the gel forming liquid to form a gel in the at least one chamber.

Furthermore, in accordance with an embodiment of the present invention, the gel forming liquid is selected from, a liquefied form of the gel capable of gelling to form the gel, and a liquid gel precursor including reactants capable of reacting to form the gel.

Finally, in accordance with an embodiment of the present invention, the at least one resonating part of the one or more resonating units forms part of the walls of the at least one sealed chamber.

DETAILED DESCRIPTION OF THE INVENTION

The present invention discloses novel resonating sensors in which the vibratable part of the sensor is protected from deposition of undesirable materials or cells or tissues or other undesirable deposits, and methods for constructing such protected sensors.

In accordance with one possible embodiment of the present invention, the vibratable resonating part or parts of the resonating sensor are protected by using a protective compliant membrane coupled to the vibratable part(s) of the sensor(s) by a non-compressible medium. For the purposes of the present application, the term non-compressible medium defines any suitable substantially non-compressible liquid or any suitable substantially non-compressible gel. The physical variable to be measured (such as, but not limited to, pressure and temperature) is transferred to the vibratable part(s) of the resonating sensor with minimal attenuation while the compliant membrane prevents the accumulation or deposition of extraneous substances on the vibratable part of the sensor.

It is noted that, while the particular examples described in detail hereinafter and illustrated in FIGS. 1-4 are adapted for passive ultrasonic sensors, the method of protection of a resonating sensor may be similarly applied to any type of resonating sensors including resonating parts which may be detrimentally affected by the deposition or accumulation of extraneous substance(s) or material(s) or tissues or cells on the surface of the resonating part of the sensor. Thus, the method of protection of resonating sensors of the present invention is a general method and may be applied to many different types of resonating sensors, such as, but not limited to, active or passive acoustic resonating sensors, active or passive ultrasonic sensors, active or passive optically interrogated sensors, capacitive resonating sensors, active resonating sensors having an internal energy source or coupled to an external energy source by wire or wirelessly, or the like, as long as the sensors is interrogated using sonic energy.

Figure 8:
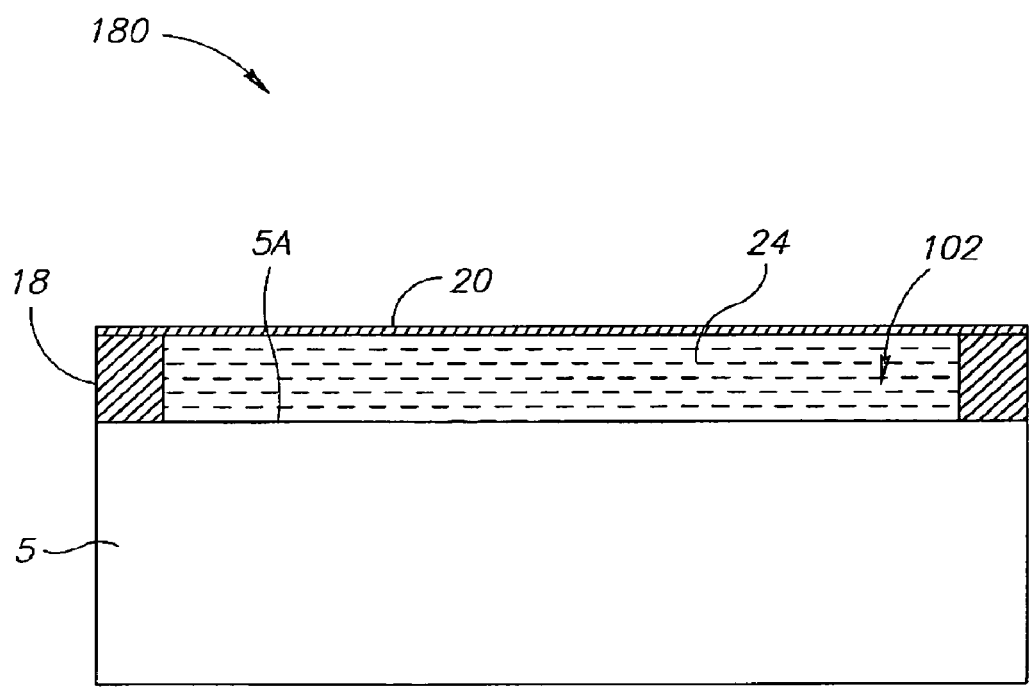
FIG. 8 is a schematic part cross-sectional diagram illustrating a general form of a protected resonating sensor in accordance with an embodiment of the present invention.

Thus, as will be appreciated by those skilled in the art, the methods of protecting resonating sensors disclosed herein may be applied to any suitable type of resonating sensor known in the art which has one or more resonators or resonating parts exposed to a measurement environment or medium (see FIG. 8 for a schematic illustration of a protected resonating sensor).

Reference is now made to FIG. 1 which is a schematic cross-sectional view of a protected passive ultrasonic pressure sensor having multiple vibratable membranes, in accordance with an embodiment of the present invention.

The protected sensor 10 may include a sensor unit 82. The sensor unit 82 may include a first recessed substrate layer 12 and a second layer 14 sealingly attached to the first recessed layer 12. The first recessed layer 12 has a plurality of recesses 16 formed therein. While only three recesses 16 are shown in the cross-sectional view of FIG. 1, the protected sensor 10 may be designed to include any practical number of recesses (such as for example, one recess, two recesses, three recesses or more than three recesses 16). For example, the protected sensor 10 may include nine recesses 16 arranged three rows having three recesses per row (not shown in FIG. 1).

The first recessed substrate layer 12 and the second layer 14 may be made from any suitable material such as, but not limited to, a metal, silicon, Pyrex®, boron nitride, glass, or the like. Preferably (but not obligatorily), the first substrate layer 12 is made from a material such as silicon, Pyrex® or another suitable material that is amenable to machining using standard lithography methods known in the art (such as, for example, the forming of the recesses 16 in the first substrate layer 12 using conventional masking, photoresist application and etching methods, and the like). However, other machining or micromachining, or processing methods known in the art may also be used with appropriate selection of other desired materials for constructing the sensor units of the present invention.

The second layer 14 is sealingly attached or glued or affixed to the first layer 12 to form a plurality of sealed sensor unit chambers 17. As disclosed hereinabove, while the cross-sectional view of FIG. 1 shows only three sealed sensor unit chambers 17, there may or may not be more than three sealed sensor unit chambers in the protected sensor 10. For example, the protected sensor 10 may include nine sealed sensor unit chambers 17 arranged three rows each row having three chambers per row, in an arrangement similar to the multi-membrane sensor disclosed in detail in FIGS. 2 and 3 of U.S. patent application to Girmonsky et al., Ser. No. 10/828,218. The parts labeled 14A, 14B and 14C of the second layer 14 lying above the recesses 16 represent the vibratable membranes 14A, 14B and 14C of the protected sensor 10.

The protected sensor 10 may also include a spacer 18 attached to the sensor unit 82. The spacer 18 may be made from a rigid material such as, but not limited to, a metal, silicon, boron nitride, glass, or a polymer based material such as SU8® epoxy based photoresist (commercially available from MicroChem Corp., MA, U.S.A), or the like.

While the spacer 18 is shown as a separate component sealingly attached or glued to the second layer 14 of the sensor unit 82, in other possible embodiments the spacer 18 may be formed as a part of the second layer 12, or as a part of the first recessed layer 12. The protected sensor 10 also includes a compliant member 20 sealingly attached to the spacer 18 to form a sealed chamber 22 (by using a suitable glue or any other suitable method known in the art for sealingly attaching the compliant member 20 to the spacer 18). The compliant member 20 may be made from a thin membrane that has a high compliance. For example, in accordance with one implemented embodiment of the present invention, the compliant member 20 may be a Kapton® membrane having a thickness of about nine micrometers.

It is noted that when selecting the material from which the compliant member 20 is made, care should be taken to ensure that the acoustic impedance of the selected material (for propagation of ultrasound) is matched to the acoustic impedance of the medium 24, and to the acoustic impedance of the material or medium or tissue in which the sensor is disposed. This matching may prevent excessive reflection of ultrasound at the interface between the medium in the measurement environment and the compliant member 20 and at the interface between the compliant member 20 and the medium 24. While it may not always be possible to obtain the best impedance match for each and every application due to practical constraints in the choice of the material(s) forming the non-compressible medium 24 and the compliant member 20 and compromises may have to be made, such impedance matching should be carefully considered in the design and implementation of the protected sensors of the present invention in order to improve sensor performance.

In accordance with additional embodiments of the present invention, the compliant member 20 may also be made from suitable Polyurethane rubbers, such as, but not limited to 6400 Polyurethane rubber or 6410 Polyurethane rubber, commercially available from Ren Plastics, USA. The compliant member 20 may also be made from RTV60 commercially available from GE Corporation, USA. In implantable sensors, when RTV 60 is used, the RTV 60 may preferably be mixed with 1% (by weight) of tungsten powder (of approximately 1 micron mean particle size) to adjust the acoustic impedance of the compliant member 20 to a value of approximately 1.5-1.54 Mrayls (Mrayl=$10^6$ rayl), which is close to the acoustic impedance of some tissues. However, this acoustic impedance value range is not limiting and other different values of acoustic impedance of the compliant member 20 may also be acceptable, depending, inter alia on the specific application, and the detection system's sensitivity. In accordance with other embodiments of the invention, for sensors configured to be implanted in mammals or humans, the compliant member 20 may be preferably made of Echothane CPC-41 or Echothane CPC-29, both commercially available from Emerson Cummings, 604 W 182nd St., Gardena, Calif., USA. These materials have acoustic impedance values (in the ultrasound range) which exhibit an acceptable match to the acoustic impedance of water (in a sensor in which water is used as the medium 24) and tissue.

It is, however, noted that the compliant member 20 may be made from or may include any other suitable highly compliant materials known in the art, and the thickness and/or dimensions and/or composition of the compliant member 20 may be varied according to, inter alia, the sensor's specific design, the desired sensor performance, the medium in which the sensor is disposed during measurement, the pressure and temperature ranges within which the sensor needs to be operated, and other manufacturing and construction parameters and considerations.

The sealed chamber 22 may be filled with a non-compressible medium 24. The non-compressible medium 24 may be a substantially non-compressible liquid, such as but not limited to water or may be any other suitable substantially non-compressible liquid known in the art, such as, but not limited to, suitable silicon oil formulations, or the like. The non-compressible medium 24 may also be a suitable substantially non-compressible gel, such as, but not limited to, gelatin, agarose, a naturally occurring gel, a polymer based synthetic gel, a cross-linked polymer based gel, a hydrogel, a lipogel, a hydrophobic gel, a hydrophilic gel, or any other suitable type of gel known in the art. In certain applications, the protected sensor may need to be sterilized, such as, for example, in sensors that need to be implanted in a living body, or in sensors that are to be placed in sterile environments, such as in bioreactors or the like. In such applications, the medium 24 may be (but is not limited to) low vapor pressure liquids such as the Dow Corning 710® Silicon Fluid, commercially available from Dow Corning Inc., U.S.A. In other applications, the medium 24 may be a liquid such as a mixture of Fluorinert FC40 fluid and Fluorinert FC 70 fluid (about 60:40 by volume), both fluids are commercially available from 3M corporation, USA, or other suitable mixtures having different ratios of these fluids, or similar suitable Fluorinert fluids or mixtures thereof.

The use of low viscosity low vapor pressure liquids may be advantageous in such applications requiring sensor sterilization and in other applications types, because if one uses heat to sterilize the protected sensor, the use of low vapor pressure liquids as the medium 24 avoids the developing of a high pressure within the sealed chamber 22 and subsequent rupture of the compliant member 20. For similar reasons, the use of low vapor-pressure liquids or gels may be advantageous in applications in which the sensor is placed in a high temperature environment, to avoid rupture of the compliant member 20.

In applications in which the sensor is sterilized using gas phase chemical sterilization requiring exposing the sensor to a sterilizing gas under low pressure conditions it may also be preferred to use a low-vapor pressure medium within the sealed chamber 22 to prevent rupture of the compliant member 20.

The compliant member 20 may be designed and constructed such that it's resonance frequency is sufficiently low compared to the frequency range within which the vibratable membranes (such as, for example, the vibratable membranes 14A, 14B and 14C of the protected sensor 10) vibrate within the working pressure range of the protected sensor 10, to avoid the affecting of the measured signal by frequencies associated with vibrations of the compliant member 20.

Generally, the composition of the compliant member 20 should be adapted to the application by selecting a material that is suitably chemically resistant to the medium (gas or liquid) within the measurement environment to avoid excessive degradation or corrosion of the compliant member 20. In sensors that are designed to be implanted within a body in-vivo, the compliant member 20 is preferably made from (or covered with or coated with, a biocompatible material. It is noted that while Echothane—CPC-41 or Echothane—CPC-29 disclosed hereinabove may be suitable sufficiently compliant and biocompatible materials for implementing the compliant member 20, other different materials may also be used to construct the compliant member 20, such as, but not limited to, polymer based materials, biocompatible polymers, polyurethane, ethyl vinyl acetate based polymers, a Parylene®C based polymer or other suitable compliant materials.

Additionally, care should be taken in selecting the medium 24 and the material from which the compliant member 20 is made such that the reflection of the interrogating ultrasound beam from the interface between the medium in the measurement environment (not shown) and the compliant member 20 or from the interface between the compliant member 20 and the medium 24 is relatively small to avoid excessive reflection of the interrogating beam from these interfaces and a concomitant reduction in the portion of the energy of the interrogating ultrasound beam which reaches the vibratable membranes of the sensor. This may be practically achieved by selecting the material of the compliant member 20 and the medium 24 such that the acoustic impedance of the compliant membrane 20 and in the non-compressible medium 24 are reasonably close to the acoustic impedance of the medium in which the protected sensor 10 is disposed during measurement.

The sealed sensor unit chambers 17 may include a gas or a mixture of gases therewithin. When the sealed sensor unit chambers 17 are formed, the pressure within the sealed sensor unit chambers 17 is set to a value of P1. After construction of the protected sensor 10, when the protected sensor 10 is disposed in a measurement environment or medium, the pressure value in the measurement environment or medium in which the protected sensor 10 is disposed is represented by P2 (FIG. 1).

Since the medium 24 is substantially non-compressible, and the compliant member 20 has a high compliance, the pressure P2 acting on the compliant member 20 is transmitted by the compliant member 20 to the vibratable membranes 14A, 14B and 14C through the medium 24. Therefore, within a certain pressure value range, the surfaces of the vibratable membranes 14A, 14B and 14C contacting the medium 24 are subjected to practically the same pressure value P2. Thus, within the practical working pressure range of the protected sensor 10 all the vibratable membranes (including any vibratable membranes not shown in the cross-sectional view of FIG. 1) of the sensor 10 will effectively experience on their surfaces which are in contact the medium 24 the external pressure P2 acting on the protected sensor 10.

When the pressure P1 inside the sealed sensor unit chambers 17 equals the external pressure P2 in the measurement environment (P1=P2), the vibratable membranes of the sensor unit 82, (such as, for example, the vibratable 14A, 14B, and 14C) are substantially minimally stressed.

In situations in which P1≠P2, the vibratable membranes of the sensor unit 82 (such as, for example, the vibratable 14A, 14B, and 14C) are pushed by the pressure difference and become curved and therefore become stressed. The absolute value of the difference between the external pressure P2 in the measurement medium and the pressure P1 within the sealed sensor unit chambers 17 of the sensor unit 82 is ΔP=|(P2−P1)|. The stress in the vibratable membranes depends on ΔP.

The resonance frequency of the vibratable membranes of the sensor unit 82 depends on the stress in the vibratable membranes of the sensor unit 82. The resonance frequency is lowest when the vibratable membranes are minimally stressed. As the stress in the vibratable membranes increases, the resonance frequency of the vibratable membranes increases accordingly. Thus, since the resonance frequency $f_R$ of the vibratable membranes is a function of ΔP, when one determines the resonance frequency of the vibratable membranes of the sensor unit 82, it is possible to determine ΔP (the absolute value of the pressure difference) from $f_R$. By properly selecting the internal pressure P1, it is possible to determine the value of P2 from the measured resonance frequency of a calibrated passive ultrasonic sensor (such as, but not limited to the protected sensor 10 shown in FIG. 1). For example, in a simple case, if we set P1=0 (by creating vacuum in the sealed sensor unit chambers 17 of the sensor unit 82 during manufacturing of the sensor) then ΔP=P2, enabling direct determination of the pressure P2.

Thus, the protected sensor 10 may be pre-calibrated prior to use, enabling the use of a calibration curve or a look-up table (LUT) for directly obtaining the pressure P2 from the measured resonance frequency $f_R$ of the vibratable membranes (or vibratable parts, depending on the sensor type) of the passive sensor. It is, however, noted that if the sealed sensor unit chambers 17 of the sensor 10 have a non-zero internal pressure level (which is the case when the sealed sensor unit chambers 17 include a gas or gases therein and therefore have a substantial non-zero internal pressure level), the pressure may have to be corrected to take into account the effects of temperature on the gas (or gases) enclosed within the sealed sensor unit chambers 17.

Methods for measuring the resonance frequency of passive ultrasonic sensors are known in the art, are not the subject matter of the present invention, and are therefore not disclosed in detail hereinafter. Briefly, a beam of exciting ultrasound may be directed toward the sensor, the resonance frequency of the sensor may be determined from the ultrasonic signal returning from the sensor (or, alternatively, by determining the amount of energy absorbed by the sensor from the exciting beam). The interrogating ultrasonic beam may be continuous, pulsed or chirped. Such methods are disclosed, inter alia, in U.S. Pat. Nos. 5,619,997, 5,989,190 and 6,083,165 to Kaplan.

Another method for determining the resonance frequency of passive ultrasonic sensors by using the Doppler effect is disclosed in co-pending U.S. patent application Ser. No. 10/828,218 to Girmonsky et al.

It is noted that the schematic cross-sectional illustration of FIG. 1 represents a situation in which P1>P2. Because of this pressure difference, the vibratable membranes 14A, 14B and 14C are shown as having a curved shape which is convex in the direction of the compliant member 20 (it is noted that the degree of curvature of the vibratable membranes 14A, 14B and 14C is exaggerated in all the drawing figures, for clarity of illustration). In a situation in which P1=P2 (not shown), the vibratable membranes of the sensor unit 82 may or may not be flat (planar), depending, inter alia, on the sensor's structure and implementation. For example, if the sensor is coated by a layer of coating material (not shown), the vibratable membranes 14A, 14B and 14C may be curved even in cases in which P1=P2. Furthermore, in sensors in which the vibratable membranes 14A, 14B and 14C are pre-stressed at manufacturing time, the vibratable membranes 14A, 14B and 14C may be curved even in cases in which P1=P2. In a situation in which P1<P2 (not shown), the vibratable membranes of the sensor unit 82 may be curved such that the side of the vibratable membrane facing the cavity of the sealed sensor unit chamber 17 is convex.

The operability of the protected sensors of the invention was experimentally tested as follows. The experiment was performed using the multi-membrane passive ultrasonic pressure sensor 20 illustrated in FIGS. 2 and 3 of co-pending U.S. patent application Ser. No. 10/828,218 to Girmonsky et al.

The nine sensor sealed chambers 29A, 29B, 29C, 29D, 29E, 29F, 29G, 29H and 29I of the sensor (of co-pending U.S. patent application Ser. No. 10/828,218 to Girmonsky et al.) were filled with air. The non-protected sensor was placed in a controlled pressure chamber, covered with water and interrogated at various different pressure levels by an ultrasonic beam having a carrier frequency at 750 KHz and eleven sensor exciting frequencies of 72 KHz, 74 KHz, 76 KHz, 78 KHz, 80 KHz, 82 KHz, 84 KHz, 86 KHz, 88 KHz, 90 KHz and 92 KHz using the Doppler method disclosed by Girmonsky et al. in the above referenced co-pending U.S. patent application Ser. No. 10/828,218, to determine the resonance frequency of the sensor at each known pressure level in the pressure chamber.

A small stainless steel ring-like washer was then placed on a holder in the controlled pressure chamber such that the sensor was at the approximate center of the shallow opening of the washer (the height of the washer was greater than the height of the sensor. A thin compliant-film of polyethylene having a thickness of approximately 9 microns was held in a suitable frame and lowered carefully onto the washer until it was firmly attached to the upper surface of the washer. Thus, a water-filled chamber was formed by the washer and the overlying compliant polyethylene film such that the vibratable membranes of the sensor were opposed to the compliant polyethylene film, and the space formed by the washer and the attached polyethylene film was completely filled with water to form a protected sensor.

The same series of resonance frequency versus pressure measurements as performed on the non-protected sensor were performed again by repeating the measurements of the resonance frequencies for the same experimental pressure levels with the protected sensor. When the dependence of the sensor's resonance frequency on the pressure level was compared for the first and second sets of measurements (performed with the non-protected sensor and with the protected sensor, respectively), there was no substantial difference between the data set for the non-protected sensor and for protected sensor. This experiment indicates that the tested sensor may be protected by a compliant member without substantially affecting the dependence of the resonance frequency of the sensor's vibratable membranes on the external pressure.

It is noted that various structural and design modifications may be made in implementing the protective sensors of the present invention. For example, while in the protected sensor 10 of FIG. 1, the spacer 18 and the compliant member 20 are attached to the sensor unit 82, other different configurations are possible.

Figure 2:
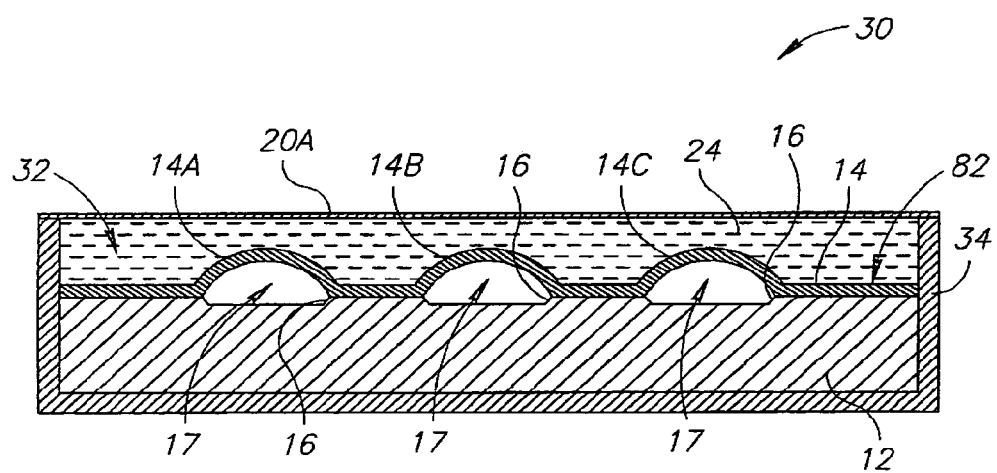
FIG. 2 is a schematic cross-sectional view illustrating a protected passive ultrasonic pressure sensor enclosed in a housing, in accordance with an additional embodiment of the present invention.

Reference is now made to FIG. 2 which is a schematic cross-sectional view illustrating a protected passive ultrasonic sensor enclosed in a housing, in accordance with an additional embodiment of the present invention.

In the protected sensor 30, the first recessed substrate layer 12, the second layer 14, the plurality of recesses 16, the sealed sensor unit chambers 17, and the vibratable membranes 14A, 14B and 14C are as disclosed in detail hereinabove for the sensor 10. The first substrate layer 12 and the second substrate layer 14 are attached together to form the sensor unit 82 which is disposed or attached within a rigid housing 34. The housing 34 may include a rigid material such as, but not limited to, a metal, a metal alloy, titanium, platinum, stainless steel, a shape memory alloy such as but not limited to NITINOL®, silicon, glass, quartz, a ceramic material, a composite material, a metallic or non-metallic nitride, boron nitride, a carbide, a metal oxide, a non-metallic oxide, a polymer based material, and combinations thereof. Such polymer based materials may include, but are not limited to, Dehrin® (commercially available from Dupont, USA), or the like.

For implantable sensors, the housing 34 may preferably be made from a biocompatible material such as titanium, platinum, or the like (including any biocompatible substances disclosed herein), or alternatively may be covered by a layer of biocompatible material (not shown) such as, but not limited to, Parylene®, or the like. A compliant member 20A is sealingly attached to the housing 34 to form a sealed chamber 32. The compliant member 20A is as described in detail hereinabove for the compliant member 20 of the sensor 10.

The sealed chamber 32 is completely filled with the substantially non-compressible medium 24, as disclosed hereinabove for the chamber 22 of the protected sensor 10. The combination of the housing 34, the compliant member 20A and the medium 24 protect the vibratable members (including, but not limited to, the vibratable members 14A, 14B and 14C illustrated in FIG. 2) of the protected sensor 30 from deposition of extraneous materials or tissues or cells, as disclosed hereinabove, without significantly attenuating the pressure transmitted to the vibratable membranes 14A, 14B and 14C of the protected sensor 30.

It is noted that, while the first recessed substrate layer 12 and the second layer 14 of the protected sensor 30 tightly fit into the housing 34 (and may also possibly be attached thereto by a suitable glue or by any other suitable attaching method known in the art), other configurations of a sensor attached within a sealed housing may also be implemented by those skilled in the art. For example, the external dimensions and/or shape of the sensor unit 82 (comprising the first recessed layer 12 and the second layer 14) may not precisely match the internal dimensions of the housing 34. Thus, in such an embodiment (not shown) the cross-sectional area of the housing of the sensor may be larger than the cross-sectional area of the unprotected sensor. Additionally, in accordance with another embodiment of the protected sensor of the present invention, more than one unprotected passive sensor may be disposed within a single protective housing.

Figure 3:
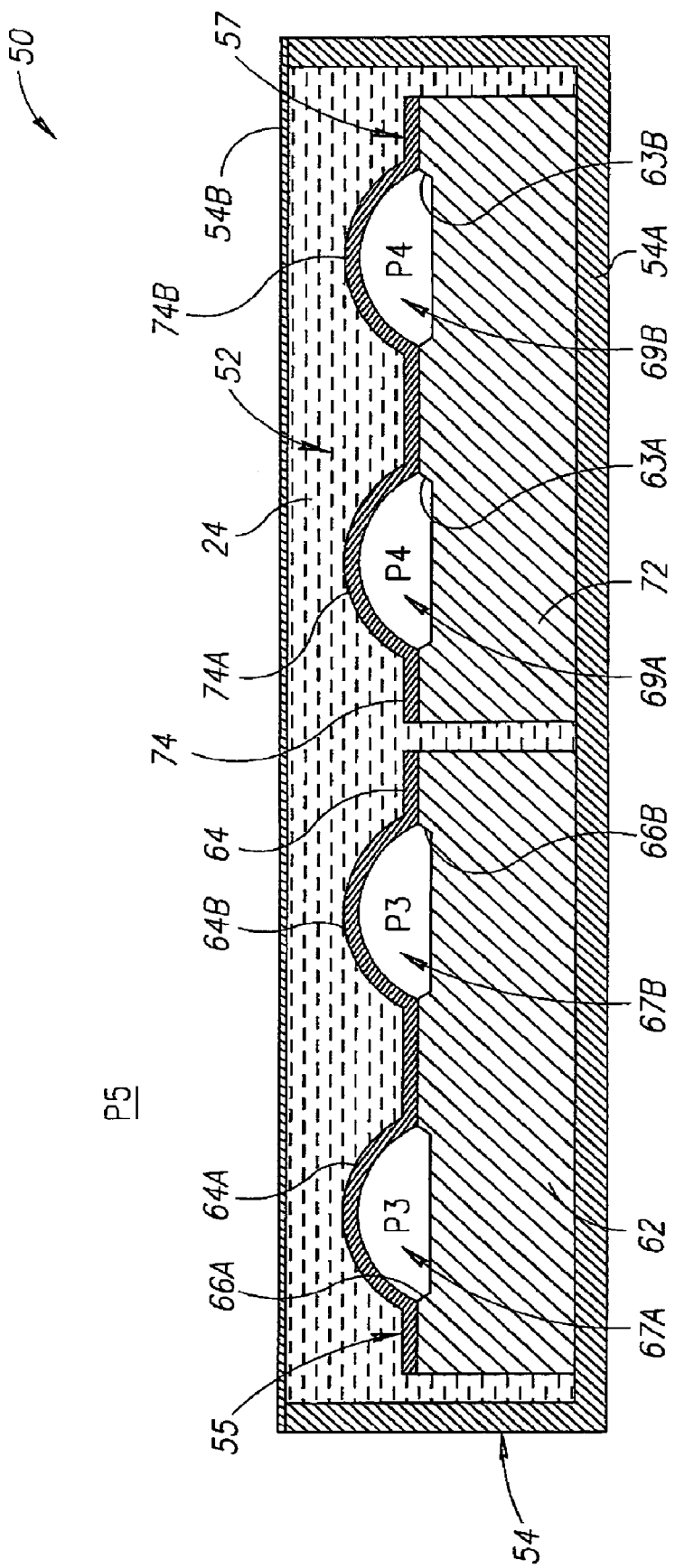
FIG. 3 is a schematic cross-sectional view illustrating a protected ultrasonic pressure sensor including two different passive ultrasonic sensor units disposed within a single protective housing, in accordance with an additional embodiment of the present invention.

Reference is now briefly made to FIG. 3 which is a schematic cross-sectional view of a protected ultrasonic sensor including two different passive ultrasonic sensor units disposed within a single protective housing, in accordance with an additional embodiment of the present invention.

The protected sensor 50 of FIG. 3 includes a protective housing 54. The housing 54 includes a housing part 54A, and a compliant member 54B. The housing part 54A may be made from any suitable material, such as, but not limited to a metal, glass, silicon, a plastic or polymer based material, or the like, as disclosed hereinabove for the housing 34 of FIG. 2. The compliant member 54B may be a highly compliant thin membrane made from Kapton®, Polyurethane, or from any other suitably compliant material, such as, but not limited to, a compliant polymer material, or the like, or any other suitable material known in the art.

The compliant member 54B may be sealingly attached to or glued to or suitably deposited on, or otherwise sealingly connected to the housing part 54A to form a sealed chamber 52. The protected sensor 50 further includes two passive ultrasonic sensor units 55 and 57. The passive ultrasonic sensor units 55 and 57 may be glued or attached or otherwise connected to the housing part 54A using any suitable attachment method or attaching materials known in the art.

The sensor unit 55 comprises a first recessed substrate layer 62 and a second layer 64. The parts 64A and 64B of the second layer 64 are vibratable membranes comprising the parts of the layer 64 which overlie recesses 66A and 66B formed within the first recessed substrate layer 62. While only two vibratable membrane parts 64A and 64B are shown in the cross-sectional view of FIG. 3, the sensor unit 55 may include one vibratable membrane or may include more than one vibratable membranes, as disclosed in detail hereinabove for the sensors 10 and 30 (of FIGS. 1 and 2, respectively). Thus, the sensor unit 55 may include any suitable number of vibratable membranes. The second layer 64 is suitably sealingly attached to the first recessed substrate layer 62 under suitable pressure conditions to form sealed sensor unit chambers (of which only sealed sensor unit chambers 67A and 67B are shown in the cross-sectional view of FIG. 3). The pressure within the sealed sensor unit chambers 67A and 67B is P3.

The sensor unit 57 comprises a first recessed substrate layer 72 and a second layer 74. The parts 74A and 74B of the second layer 74 are vibratable membranes comprising the parts of the layer 74 which overlie recesses 63A and 63B formed within the first recessed substrate layer 72. While only two vibratable membrane part 74A and 74B are shown in the cross-sectional view of FIG. 3, the sensor unit 57 may include one vibratable membrane or may include more than one vibratable membranes, as disclosed in detail hereinabove for the protected sensors 10 and 30 (of FIGS. 1 and 2, respectively). Thus, the sensor unit 57 may include any suitable number of vibratable membranes. The second layer 74 is suitably sealingly attached to the first recessed substrate layer 72 under suitable pressure conditions to form sealed sensor unit chambers (of which only sealed sensor unit chambers 69A and 69B are shown in the cross-sectional view of FIG. 3). The pressure within the sealed sensor unit chambers 69A and 69B is P4. The sensor units 55 and 57 may be manufactured such that P3=P4 or such that P3≠P4.

The sealed chamber 52 is completely filled with the substantially non-compressible medium 24 as disclosed hereinabove. The pressure P5 outside the protected sensor 50 is transmitted with minimal attenuation to the vibratable membranes of the sensor units 55 and 57 (such as, for example, the vibratable membranes 64A and 64b of the sensor unit 55 and to the vibratable membranes 74A and 74B of the sensor unit 57) through the compliant member 54B and the medium 24 as disclosed hereinabove.

The use of two (or, optionally, more than two) sensor units having different internal pressure values may be useful for providing temperature compensated pressure measurements, or for other purposes such as, but not limited to, providing an extended measurement range by including within the protected sensor two or more different pressure sensors each optimized for a particular pressure range. Additionally, one or more sensor units having similar internal sensor pressure values may be used within the same protected sensor to increase the protected sensor's signal strength, by increasing the total surface area of the vibratable membranes in the protected sensor.

It is noted that the protected sensor of the present invention may be implemented such that the protected sensor may be formed as part of a sensor anchoring device, or may be formed within a sensor anchoring device, or may be attached thereto. Such sensor anchoring device may be, but is not limited to, a sensor anchor (such as, but not limited to any of the devices disclosed in U.S. Pat. No. 6,331,163 to Kaplan), a sensor positioner, an implantable graft, any suitable part of an implantable device, a pacemaker, a defibrillator or a part thereof, an implantable electrode or a part thereof, an insertable electrode or a part thereof, an implantable catheter or a part thereof, an insertable catheter or a part thereof, a stent, a part of a stent, a guide-wire or a part thereof, an endoscopic device or a part thereof, an autonomous or a tethered endoscopic device or a part thereof, an implantable graft or other implant types, or any other suitable device which may be implanted in or inserted into in a body of any organism, animal or human patient.

It will be appreciated by those skilled in the art that the sensor anchoring devices to which the protected sensors of the present invention may be attached (or within which anchoring device such protected may be formed or included as a part thereof), are not limited to devices having the sole purpose of serving as a support or carrying platform for the protected sensor of the invention. Rather, the anchoring devices may have any other suitable structure and/or function that may or may not be related to the structure or function(s) of the protected sensor, and may also be used for other unrelated purposes besides functioning as a support for the protected sensor. For example, if a protected sensor is attached to or formed within or enclosed in an implanted electrode of a pacemaker, the electrode may function as a platform or member for carrying the protected sensor, while independently functioning as a stimulating and/or sensing electrode as is known in the art. Thus, the attachment of the protected sensors of the present invention to any device positionable in a measurement environment (or the inclusion thereof in such a device) may, but need not necessarily be associated with the functioning of the device.

Similarly, the sealed chamber of the protected sensors of the present invention may be formed within any such suitable sensor anchoring device or sensor supporting device or sensor fixating devices, or implantable grafts or other type of implant or implantable device. The sealed chamber of the protected sensors of the present invention may also be configured to comprise a part or as portion of any such suitable sensor anchoring device or sensor supporting device or sensor fixating devices, or implantable grafts or any other type of an implant or implantable device or stent, as a part of the sealed chamber.

Figure 4:
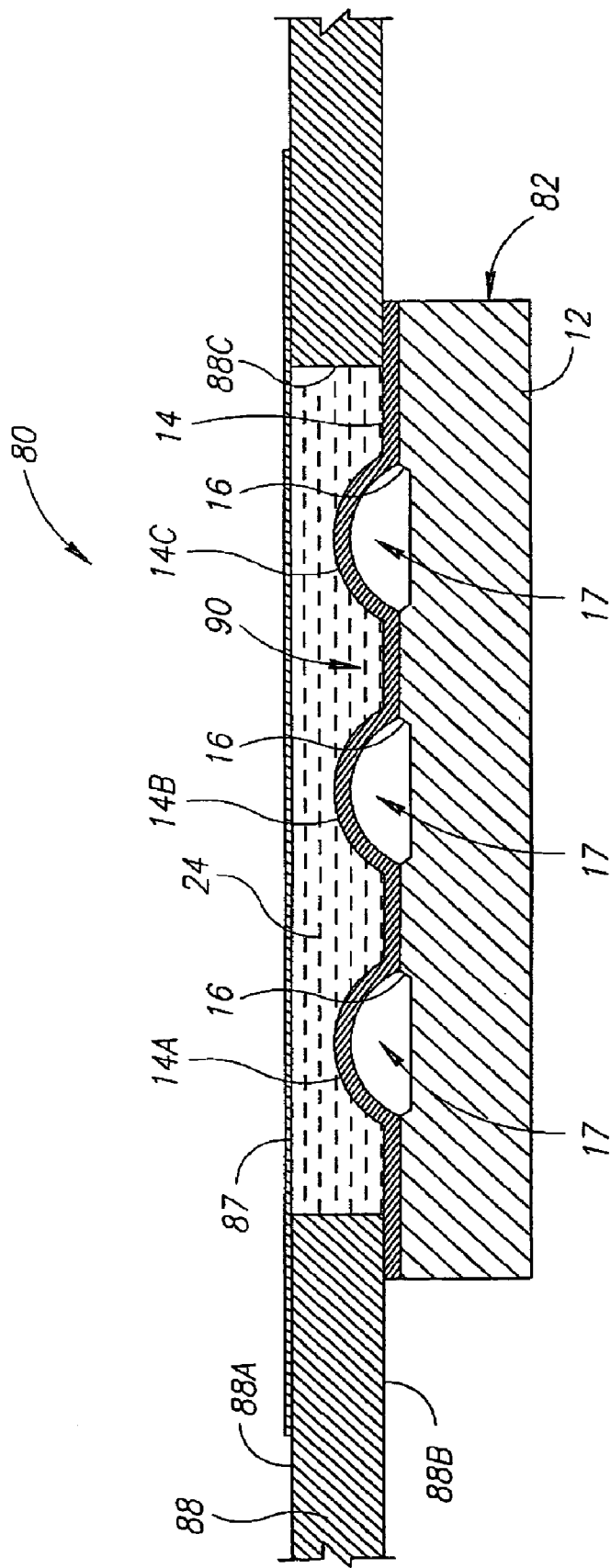
FIG. 4 is a schematic cross-sectional view illustrating part of a protected sensor constructed using a sensor anchoring device or another implantable graft or implantable device, in accordance with an additional embodiment of the present invention.

Reference is now made to FIG. 4 which is a schematic cross-sectional view illustrating part of a protected sensor constructed using a sensor anchoring device, or a sensor positioner, or an implantable graft, or an implantable device, in accordance with an additional embodiment of the present invention. The protected sensor 80 includes a sensor unit 82, an anchor 88 (only a part of the anchor 88 is illustrated in FIG. 4), and a compliant member 87. The anchor 88 has an opening 88C passing therethrough. The opening 88C is slightly smaller than the sensor unit 82. The compliant member 87 is sealingly glued or otherwise sealingly attached (using any suitable attachment method known in the art) to a first surface 88A of the anchor 88 and the sensor unit 82 is sealingly glued or otherwise sealingly attached (using any suitable attachment method known in the art) to a second surface 88B of the anchor 88.

The compliant member 87 may be a thin membrane having a high compliance constructed as disclosed in detail hereinabove for the compliant members 20, 20A and 54B (of FIGS. 1, 2, and 3, respectively). The compliant member 87 may be sealingly attached to the first surface 88A of the anchor 88 by a suitable glue or by any other sealing material or any other suitable attachment method known in the art or disclosed hereinabove, to form a sealed chamber 90. The sealed chamber 90 is completely filled with the substantially non-compressible medium 24 as disclosed hereinabove.

The sensor unit 82 may include the recessed substrate layer 12, and the second layer 14 constructed and operative as disclosed in detail hereinabove for the sensor unit 82 of the protected sensors 10 and 30 (of FIGS. 1 and 2, respectively).

Figure 5:
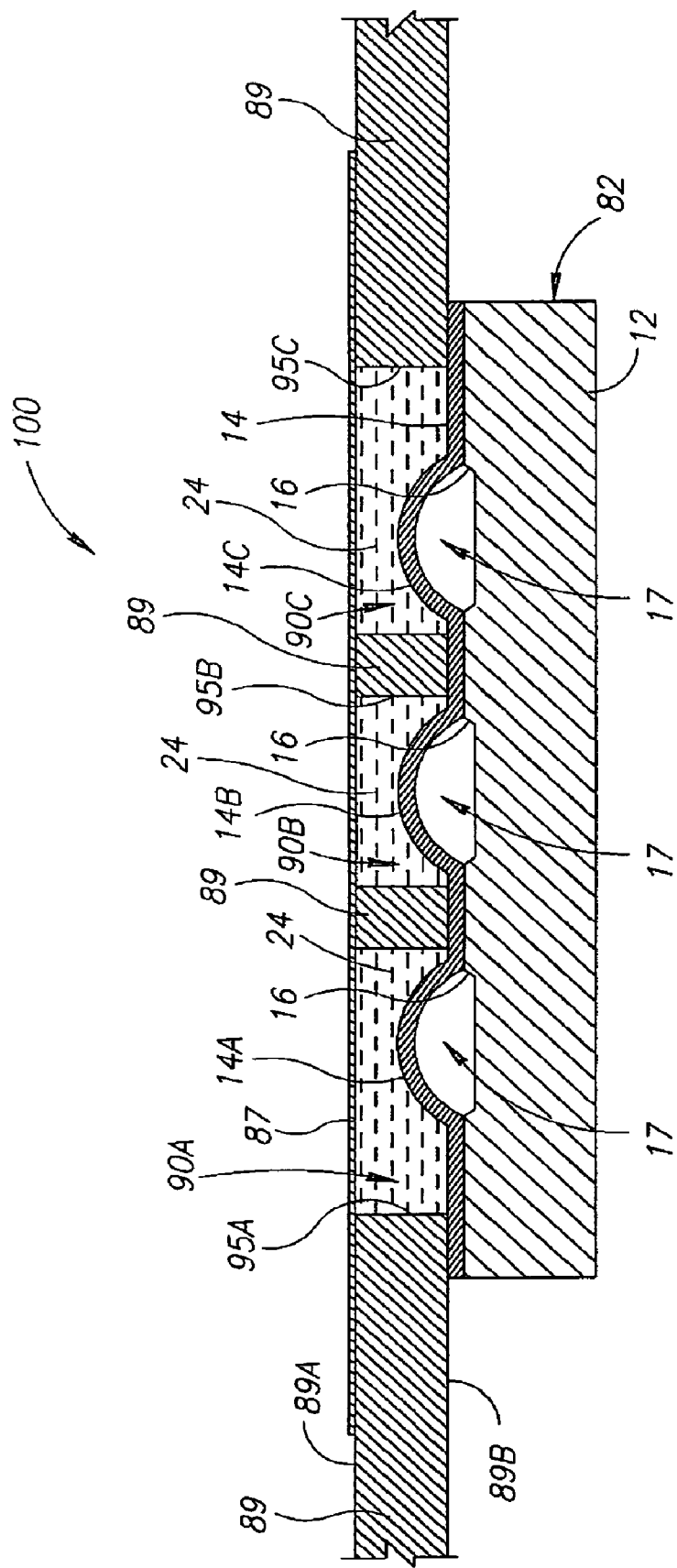
FIG. 5 is a schematic cross-sectional view illustrating part of a protected sensor having multiple sealed chambers constructed within a sensor anchoring device or implantable graft or implantable device, in accordance with another embodiment of the present invention.

Reference is now made to FIG. 5 which is a schematic cross-sectional view of part illustrating a protected sensor having multiple sealed chambers constructed within a sensor anchoring device or implantable graft or implantable device, in accordance with another embodiment of the present invention. The protected sensor 100 includes a sensor unit 82 as disclosed in detail hereinabove (with reference to FIG. 4), an anchor 89 (only a part of the anchor 89 is illustrated in FIG. 5), and a compliant member 87. The anchor 89 has a plurality of openings 95A, 95B and 95C passing therethrough. The compliant member 87 is sealingly glued or otherwise sealingly attached (using any suitable attachment method known in the art) to a first surface 89A of the anchor 89 and the sensor unit 82 is sealingly glued or otherwise sealingly attached (using any suitable attachment method known in the art) to a second surface 89B of the anchor 89.

The compliant member 87 may be a thin membrane having a high compliance constructed as disclosed in detail hereinabove for the compliant members 20, 20A and 54B (of FIGS. 1, 2, and 3, respectively). The compliant member 87 may be sealingly attached to the first surface 89A of the anchor 89 by a suitable glue or sealer, or by any other sealing material or any other suitable attachment method known in the art or disclosed hereinabove, to form a multiplicity of sealed chambers 90A, 90B and 90C. The sealed chamber 90 is completely filled with the substantially non-compressible medium 24 as disclosed hereinabove.

The sensor unit 82 may be constructed and operated as disclosed in detail hereinabove with reference to FIG. 4. It is noted that while the protected sensor 100 of FIG. 5 includes three sealed chambers (90A, 90B and 90C), the protected sensor 100 may be implemented having any suitable number of sealed chamber and any suitable number of vibratable members.

It is noted that, for the sake of clarity of illustration, the dimensions of the vibratable membranes 14A, 14B and 14C, and of the parts of the compliant member 87 overlying the chambers 90A 90B and 90C, respectively do not necessarily represent the true dimensions of these parts and the ratio of their cross-sectional areas (such as, for example the ratio of the surface area of the vibratable membrane 14B to the area of the part of the compliant member 87 overlying the chamber 90B). Preferably, the surface area of the part of the compliant member overlying the chambers 90A, 90B and 90C are substantially greater than the surface area of the corresponding vibratable membranes 14A, 14B and 14C to allow proper sensor operation. It is noted that in all the other drawing figures, due to the schematic nature of the drawings, the scale and the ratio of the surface area of the part of the compliant member overlying a specific chamber to the surface area of the vibratable member or membrane included in that chamber may not necessarily be accurately represented.

It will be appreciated by those skilled in the art that the protected sensors of the present invention are not limited to sensors including a single vibratable member, or a single resonating sensor within a single sealed chamber. Thus, protected sensors including more than one sensor or more than one vibratable member within a sealed chamber are within the scope of the present invention.

For example, a protected sensor may be constructed in which there are multiple sealed chambers, each of the multiple sealed chambers may have more than one resonating sensors therewithin. Similarly, a protected sensor may be constructed in which there are multiple sealed chambers, each of the multiple sealed chambers may have more than one vibratable member therewithin. Additionally, a protected sensor may be constructed in which there is a single sealed chamber, in which more than one resonating sensors or more than one vibratable member may be disposed.

Figure 6:
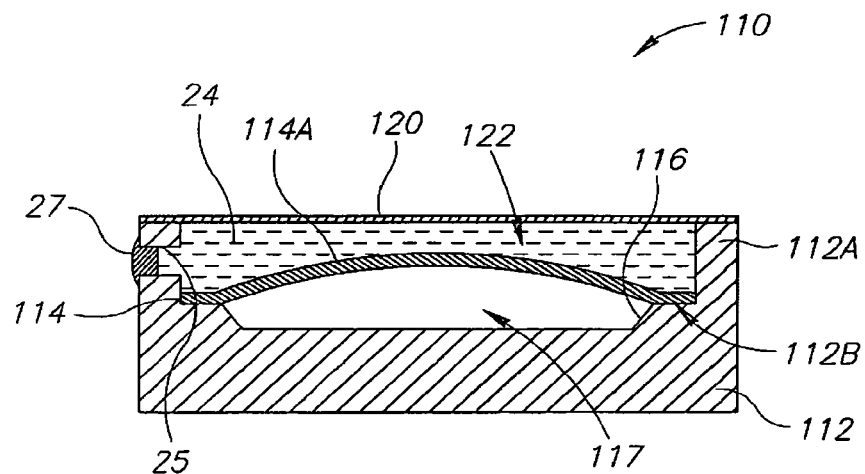
FIG. 6 is a schematic cross-sectional view illustrating a protected passive ultrasonic pressure sensor having a single vibratable membrane, in accordance with an embodiment of the present invention.

Reference is now made to FIG. 6 which is a schematic cross-sectional view illustrating a protected passive ultrasonic pressure sensor having a single vibratable membrane, in accordance with an embodiment of the present invention.

The sensor 110 may include a substrate 112, a second layer 114, a compliant member 120 and a substantially non-compressible medium 24 filling a sealed chamber 122. The second layer 114 may be glued or sealingly attached to a surface 112B of the substrate 112, as disclosed in detail hereinabove. The substrate 112 has a recess 116 formed therein. The substrate 112 has a ridge 112A protruding above the level of the surface 112B. The ridge 112A may (optionally) have an opening 25 passing therethrough. The opening 25 may be used for filling the chamber 122 with the medium 24, as disclosed in detail hereinafter. If the ridge 112A has one or more openings 25 formed therein, the opening(s) 25 may be closed after filling of the medium 24 by applying a suitable sealing material 27. The sealing material 27 may be any suitable sealing material known in the art, such as but not limited to, RTV, silicon based sealants, epoxy based sealing materials, or the like, as is disclosed in detail hereinafter.

The second layer 114 may be glued or sealingly attached to the surface 112B of the substrate 122 to form a sealed sensor unit chamber 117. A part of the second layer 114 that overlies the recess 116 forms a vibratable member 114A that may vibrate in response to mechanical waves (such as, for example, ultrasound waves) reaching the sensor 110. The sealed sensor unit chamber 117 may include a gas or a mixture of gasses having a pressure level therein, as disclosed hereinabove. The pressure level within the sealed sensor unit chamber 117 may be a zero pressure level (if the chamber 117 is evacuated of any gas) or may be a non-zero pressure level (if the chamber 117 includes a certain amount of a gas or gases). The compliant member 120 may be attached or glued or sealingly attached (using any suitable attaching or sealing or gluing method known in the art) to the ridge 112A of the substrate 112 to form a chamber 122. The chamber 122 is preferably completely filled with the substantially non-compressible medium 24. The material composition of the parts of the sensor 110 may be similar to those disclosed hereinabove for other sensors.

It is noted that while the protected sensor 110 of FIG. 6 has a single sealed chamber 122 filled with the medium 24, a single sealed sensor unit chamber 117 and a single vibratable member 114A, other embodiments of the sensor may include more than one vibratable member, and/or more than one sealed sensor unit chamber, and/or more than one sealed chamber filed with the medium 24, as disclosed in detail hereinabove for other sensor embodiments.

It is noted that the anchor 88 (of FIG. 4) and the anchor 89 (of FIG. 5) may be any suitable part of any device (including, but not limited to, an implantable or an insertable device) to which the sensor unit 82 may be suitably attached in the configuration illustrated in FIG. 4, or in any other suitable configuration for forming a sealed chamber filled with a non-compressible medium. For example, the anchor 88 and the anchor 89 may be, but are not limited to, any suitable sensor support devices or sensor fixation devices, such as but not limited to the sensor supporting and/or sensor fixating devices disclosed in U.S. Pat. No. 6,331,163 to Kaplan. The anchor 88 and the anchor 89 may be, but are not limited to, any suitable part of a graft, a stent, an implantable electrode, an insertable electrode, a pacemaker, a defibrillator, a guide-wire, an endoscope, an endoscopic device, an autonomous endoscopic device or autonomous endoscopic capsule, a tethered endoscopic device or capsule, an implantable or an insertable drug or therapeutic substance releasing device or chip or pump, or any other implantable or insertable device known in the art, as disclosed in detail hereinabove.

Furthermore, if the protected sensors of the present invention are formed as a self contained protected sensor (such as, but not limited to, the protected sensors illustrated in FIGS. 1-3, and 6-9), the protected sensor may be suitably attached and/or glued to, and/or mounted on and/or affixed to and/or enclosed within any other suitable device which may be placed or disposed in the desired measurement environment. For example, the protected sensors of the present invention may be attached to a wall or any other internal part of a chemical or biochemical reactor (not shown) or to any measurement device or stirring device disposed in the reactor, or inside a valve or a tube or a holding tank, or the like.

Similarly, if the protected sensor is to be implanted in or inserted into an organism or animal or into a human patient, the protected sensor may be suitably attached and/or glued to, and/or mounted on and/or affixed to and/or enclosed within any suitable insertable or implantable device, including, but not limited to, a suitable graft, a stent, an implantable electrode, an insertable electrode, a pacemaker, a defibrillator, a guide-wire, an endoscope, an endoscopic device, an autonomous endoscopic device or autonomous endoscopic capsule, a tethered endoscopic device or a tethered capsule, an implantable or an insertable drug or therapeutic substance releasing device or chip or pump, or any other implantable or insertable device known in the art, and as disclosed in detail hereinabove.

Figure 7:
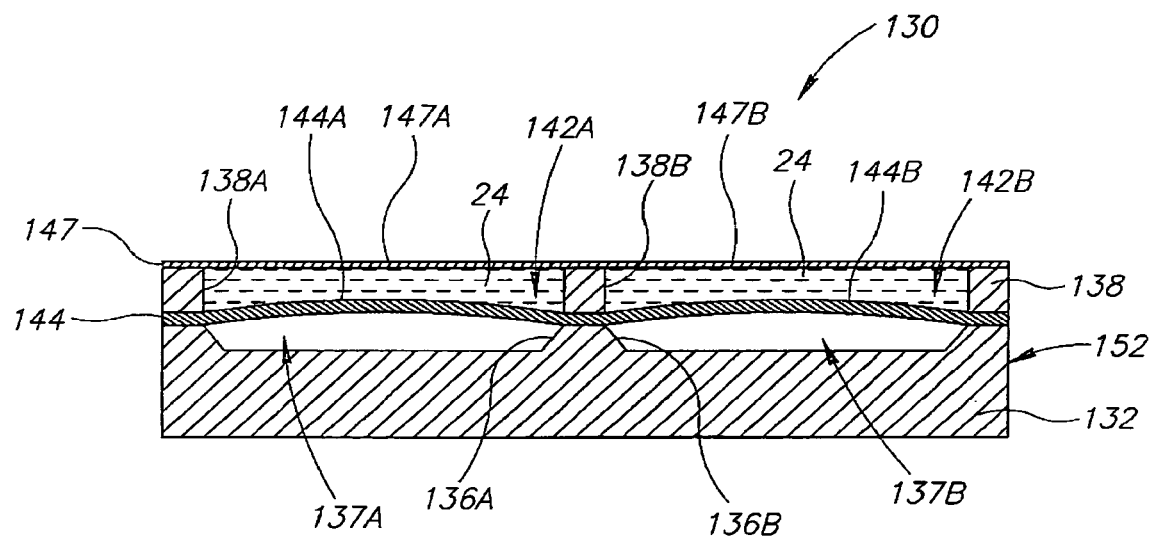
FIG. 7 is a schematic cross-sectional view illustrating a protected passive ultrasonic pressure sensor with multiple vibratable membranes having multiple sealed chambers formed within a spacer, in accordance with yet another embodiment of the present invention.

Reference is now made to FIG. 7 which is a schematic cross-sectional view illustrating a protected passive ultrasonic pressure sensor with multiple vibratable membranes having multiple sealed chambers formed within a spacer, in accordance with yet another embodiment of the present invention.

The protected sensor 130 may include a passive ultrasonic pressure sensor unit 152, a spacer member 138, a compliant member 147 and a substantially non-compressible medium 24. The spacer member 138 has two openings 138A and 138B formed therein. The sensor unit 152 includes a substrate 152 having two recesses 136A and 136B formed therein. The sensor unit 152 also includes a second layer 144 sealingly attached or bonded or glued to the substrate 132 to form two separate sealed sensor unit chambers 137A and 137B. The sealed sensor unit chambers 137A and 137B may be filled with a gas or a mixture of gases, or may have a vacuum therein as disclosed hereinabove. The parts of the layer 144 overlying the recesses 136A and 136B form two vibratable membranes 144A and 144B, respectively. The spacer member 138 may be sealingly attached or glued or bonded to the layer 144. The compliant member 147 may be suitably or sealingly attached or glued or bonded to the spacer member 138 to form two sealed chambers 142A and 142B. The sealed chambers 142A and 142B may, preferably, be completely filled with a substantially non-compressible medium 24, using any suitable filling method known in the art.

The part 147A of the compliant member 147 may protect the vibratable membrane 144A from deposition of extraneous material as disclosed in detail hereinabove. Similarly, the part 147B of the compliant member 147 may protect the vibratable membrane 144B from deposition of extraneous material.

It is noted that while the protected sensor 130 of FIG. 7 has two sealed chambers 142A and 142B filled with the medium 24, a single sealed sensor chamber 117 and a single vibratable member 114A, other embodiments of the sensor may include more than one vibratable member, and/or more than one sensor sealed chamber, and/or more than one sealed chamber filed with the medium 24, as disclosed in detail hereinabove for other sensor embodiments.

It is noted that different variations of components or functions of the illustrated embodiments are interchangeable between the different embodiments of the protected sensor assemblies as illustrated in FIGS. 1-8, and that many different permutations and variations thereof are possible and are included within the scope of the present invention.

It is noted that the protected sensors of the present invention, including but not limited to the sensors disclosed hereinabove and illustrated in FIGS. 1-8, may be constructed or assembled using various different methods. For example, turning briefly to FIG. 6, the sensor 110 may be made by first forming the substrate 112 and the recess 166 and opening 25 therein using any suitable photolithographic method known in the art (such as, but not limited to, standard lithographic masking, photoresist and wet etching methods applied to a silicon wafer or other suitable substrate, or by other suitable micromachining methods), the second layer 114 may then be glued or bonded or attached to the substrate layer 112 in a suitable pressure chamber to ensure the desired pressure level in the sensor sealed chamber 117.

The compliant member 120 may then be sealingly attached or glued or bonded to the ridge 112A of the substrate 112. The sensor 110 may then be placed in a suitable vacuum chamber (not shown) and allowing sufficient time for equilibration of pressure to form a suitable vacuum within the chamber 122 (which is not yet sealed at this stage). After the chamber 122 has a high vacuum therein, the sensor may be immersed in the medium 24 (for this vacuum assisted filling method the medium 24 should be a low vapor pressure liquid, such as but not limited to Dow Corning 710® Silicon Fluid disclosed hereinabove, or any other suitable low vapor pressure fluid or liquid known in the art) such as, for example, by introducing the medium 24 into the vacuum chamber to a suitable level such that the opening 25 is completely covered by the medium 24.

After, the opening 25 is covered by the medium 24, the pressure in the vacuum chamber in which the sensor 10 is disposed may be increased (for example, by opening the vacuum chamber to atmospheric pressure) as the pressure acting on the medium 24 disposed within the vacuum chamber is increased, the medium 24 will be forced into the empty space of the chamber 122 until the chamber 122 is completely filled with the medium 24. After the chamber 122 is filled with the medium 24, the sensor 110 may be cleaned (if necessary) and the opening 25 may be sealingly closed with the sealing material 27 to complete the sealing of the chamber 122. The sealing material 27 may be any suitable sealing material known in the art, as disclosed in detail hereinabove.

It is noted that it may also be possible, in accordance with another embodiment of the invention, to inject the medium 24 into the chamber 122 of the sensor 110 through the opening 25 by using a fine needle or any other suitable injecting device, which may be followed by application of the sealing material to seal the opening 25.

It is noted that the methods for filling the chamber 122 (or any other chamber of a protected sensor being used) with the medium 24 are not limited to using non-compressible liquids but may also be applied when using various types of gels. For examples when using gelatin it is possible to use the methods described hereinabove for filling the sensor by applying the gelatin while it is in a liquid fluid state prior to solidification by using a heated liquefied gelatin solution. In such cases it may be advantageous to warm the sensor that is being filled to a suitable temperature to prevent or delay solidification of the gel. When using hydrogels or other gel types, time is required for gelling, so it is possible to fill the chamber of the protected sensor before gelling occurs. In another example, it may be possible to use an alginate based gel (such as, for example, a liquid sodium alginate solution) and induce gel formation by adding calcium ions, as is known in the art.

It may also be possible to use other liquid compositions or liquid gel precursors that may form a gel after filling or injecting into the chamber 122 as disclosed hereinabove. For example, in accordance with an embodiment of the present invention it is possible to use a mixture of monomer(s) and a suitable catalyst and/or polymerizing agent and/or cross-linking agent which may chemically react to slowly produce a suitable gel. The mixture of the monomer and cross-linker may be injected or otherwise introduced into the chamber of the sensor (such as, but not limited to, the chamber 122 of the sensor 110) by any of the methods described hereinabove while still in the liquid state and may then polymerize to for the gel in the chamber.

In applications for non implanted sensors it may be possible to use gels such as polyacrylamide gels, as is known in the art. Such gels may be formed by polymerizing acrylamide or acrylamide derivative monomers using a polymerization catalyst or initiator (such as, for example, persulfate, or the like) and/or suitable cross-linking agents (for example bisacrylamide based cross-linkers). For applications using implantable sensors other, more biocompatible gels may have to be used, such as gelatin, or any other suitable bio-compatible or hemocompatible hydrogel or lipogel, or hydrophobic gel, or hydrophilic gel, known in the art.

It is further noted that other different methods for constructing the protected sensor may be also used. Such methods may include methods in which the compliant member is attached to or formed on the protected sensor after the placement of the substantially non-compressible medium in the sensor. Briefly returning to FIG. 1, the sensor 10 may be constructed as follows. First the recessed substrate layer 12 may be attached to the second layer 14 in a vacuum chamber (not shown) to form the sensor unit 82 in a way similar to the way disclosed hereinabove for the sensor 110 of FIG. 6, or as disclosed in the above referenced co-pending U.S. patent application, Ser. No. 10/828,218 to Girmonsky et al. After the sensor unit 82 is made, the spacer 18 may be attached or glued to the sensor unit 82 to form part of the chamber 22 (which at this stage is not yet a sealed chamber). The medium 24 may then be introduced into the formed part of the chamber 22 and the compliant member 20 may then be suitably sealingly attached or bonded to the spacer 18, using any attaching or gluing or bonding method known in the art, to seal the medium 24 and to complete the sealed chamber 22. This method may be applied when the medium 24 is a liquid or a gel. In cases where a gel is used, the gel may be introduced into the chamber 22 in a pre-gelled liquid form or as a monomer/cross-linker mixture as disclosed hereinabove.

Yet another method for constructing the protected sensor (described, by way of example, with respect to the sensor 10 of FIG. 6, but generally applicable to many of the other sensors disclosed and illustrated herein) may use chemical vapor deposition methods (or possibly other different methods known in the art to directly form and attaché a compliant member to the sensor unit. Turning again to FIG. 1, the sensor 10 may also be constructed as follows. First the recessed substrate layer 12 may be attached to the second layer 14 in a vacuum chamber (not shown) to form the sensor unit 82 in a way similar to the way disclosed hereinabove. After the sensor unit 82 is made, the spacer 18 may be attached or glued to the sensor unit 82 to form part of the chamber 22 (which at this stage is not yet a sealed chamber). The medium 24 may then be introduced into the formed (yet open) part of the chamber 22. The compliant member 20 may then be directly deposited on the medium 24 and on the spacer 18 by forming the compliant member in-situ using a suitable chemical vapor deposition (CVD) method. For example, if the compliant member 20 is to be made from Parylene®, a suitable layer of Parylene®C may be sealingly deposited or formed upon the medium 24 and the spacer 18 using standard CVD methods. In this case, the layer of Parylene®C formed over the substantially non-compressible medium 24 and attached to the upper surface of the spacer 18 comprises the compliant member 20. In such a case, if the CVD is performed below atmospheric pressure, the medium used in the sealed chamber must have a low vapor pressure.

It is noted that the different methods disclosed for constructing the protected sensors may in principle be applied to construct any of the protected sensors disclosed hereinabove and illustrated in the drawing figures with suitable modifications. For example, if the chamber 22 of sensor 10 of FIG. 1 needs to be to be filled with the medium 24 through an opening, one or more openings (not shown) may be made in the spacer 18.

Similarly, suitable openings (not shown) may need to be made in the housing 34 of the protected sensor 30 (of FIG. 2) or in the housing 54 of the protected sensor 50 of FIG. 3) or in any other suitable part of the protected sensors disclosed herein in order to enable the introducing of the substantially non-compressible medium 24 into the relevant chamber(s) of the protected sensor that is being filled.

In accordance with another embodiment of the invention, one or more openings (not shown) suitable for introducing the medium 24 may (optionally) be formed in suitable parts of the anchoring members 88 and/or 89 or in the sensor unit 82 to allow filling of the medium 24 therethrough. Such openings may be sealed by a sealing material after the filling is completed, as disclosed in detail with respect to the opening 25 of the sensor 110 of FIG. 6). It is therefore noted that if the substantially non-compressible medium is introduced into the sealed chamber of the protected sensor of the present invention through one or more openings, such an opening or such openings (not shown) may be formed in any selected or desired part of the sensor, such as, but not limited to, the sensor's housing or the sensor anchoring device (if user) or the spacer (if used) or through any suitable parts of the body of the sensor unit used. Such openings may be located at positions that will not compromise the sensor's operation as will be clear to the person skilled in the art.

Furthermore, if the protected sensor includes multiple sealed chambers (such as, for example, the chambers 90A, 90B and 90C of the protected sensor 100 of FIG. 5) additional openings (not shown) may have to be made in suitable parts of the sensor or sensor unit or spacer or anchoring device if needed.

It will be appreciated by those skilled in the art that the different methods disclosed herein for assembling or constructing the protected sensors of the invention, are given by way of example only, are not obligatory, and that other different methods of construction and/or assembly and or filling of the disclosed protected sensors my be used, as is known in the art. Such methods may include, but are not limited to, any suitable lithographic methods, etching methods, masking methods, semiconductor manufacturing methods, micromachining methods, imprinting methods, embossing methods, printing methods, layer forming methods, chemical vapor deposition methods, bonding methods, gluing methods, sealing methods, and the like.

It will be appreciated by those skilled in the art that the embodiments of the protected sensor described hereinabove and illustrated in FIG. 4 is not limited to the forms of sensor anchors or sensor fixation devices or stent parts shown above or in U.S. Pat. No. 6,331,163 to Kaplan. Rather, many different modifications of the protected sensor of the invention may be implemented by those skilled in the art. For example, a non-limiting list of possible implementations may include implementations in which the anchor 88 may be part of an implantable graft (for example a tube-like Gortex® graft, as is known in the art), or may be part of an implantable electrode of a pacemaker device or a defibrillator, or of any other suitable device which may be implanted in a blood vessel, or in any other part of a cardiovascular system, or intra-cranially, or within any of the ventricles of the brain, or in the central canal of the spinal cord, or in the heart, or in any other body cavity or lumen thereof, as is known in the art.

Reference is now made to FIG. 8 which is a schematic part cross-sectional diagram illustrating a generalized form of a protected resonating sensor in accordance with an embodiment of the present invention.

The protected sensor 180 of FIG. 8 includes a resonating sensor unit 5, a spacer 18, a compliant member 20 and a non-compressible medium 24. The resonating sensor unit 5 may be any type of resonating sensor known in the art which has one or more resonators or resonating parts exposed to a measurement environment or medium, such as, but not limited to, any of the resonating sensors disclosed hereinabove or known in the art. The resonator part 5A of the resonating sensor unit 5 schematically represents the part of the resonator (or resonators) of the resonating sensor unit 5 which would have been exposed to the measurement environment or medium in a non-protected resonating sensor unit 5.

The protected sensor 180 may include a spacer 18 suitably sealingly attached or glued to the sensor 5 as disclosed in detail hereinabove for the spacer 18 of FIG. 1. The protected sensor 180 may also include a compliant member 20 as disclosed in detail hereinabove for the sensor 10 of FIG. 1. The compliant member 20 is suitably sealingly attached to the spacer 18 to form a sealed chamber 102. The sealed chamber 102 is completely filled with a non-compressible medium 24 as described in detail hereinabove for the sensors 10, 30 and 80 (of FIGS. 1, 2 and 4, respectively).

The physical variable to be measured by the protected sensor 180 (such as, but not limited to, pressure, temperature or the like) is transmitted with minimal attenuation through the compliant member 20 and the non-compressible medium 24 to the part 5A of the resonating sensor unit 5, as disclosed in detail for the other passive ultrasonic sensors disclosed hereinabove. The compliant member 20 and the spacer 18 prevent the deposition of substance(s) or cell(s) or tissue(s) or other undesirable extraneous material from entering the sealed chamber 102 and from being deposited on or otherwise attached to the part 5A of the resonating sensor unit 5. The resonating part or parts of the sensor unit 5 (not shown in detail in FIG. 8) are thus protected from any such substance(s) or cell(s) or tissue(s) or other undesirable extraneous material found in the measurement environment or measurement medium which may improve the ability of the protected sensor 180 to maintain stability and accuracy of measurement over time.

It is noted that while in the embodiment of the protected sensor 80 illustrated in FIG. 5, the sealed chamber 102 including the medium 24 is constructed by using the spacer 18, it may be possible, in accordance with another embodiment of the protected sensor, to attach the compliant member 20 to a suitably formed part (not shown) of the sensor unit 5, such as a raised circumferential ridge (similar, but not necessarily identical to the ridge 112A of the sensor 110 of FIG. 6) formed as part of the sensor unit 5.

It is noted that in cases in which the sensor unit 5 is a resonating sensor for sensing the concentration of a chemical species in the measurement medium, the compliant member 20 and the non-compressible medium 24 should be carefully selected such that the compliant member 20 is made from a material which is suitably permeable to the chemical species being measured and that the non compressible medium 24 is selected such that the chemical species to be measured may be capable of diffusing in the selected medium 24, or may be capable of being transported through the medium 24 (for example, by including in the medium 24 a suitable transporter species or transporting molecule which is compatible with the medium 24, as is known in the art) to reach the part of the sensor unit 5 (possibly included in the part 5A of the sensor unit 5) which is sensitive to the concentration of the chemical species being measured.

It will be appreciated by those skilled in the art that the protected pressure sensors of the present invention are not limited to using only the type of compliant members disclosed hereinabove. Rather, the protected pressure sensors of the present invention may also be implemented by using differently configured compliant members. Such mechanically compliant members may be configured or shaped in many different ways (as is known in the art) to enable the efficient transmission of pressure from the region of measurement to the vibratable membranes or vibratable members of the sensor used. The compliant member also has to be sufficiently compliant so as not to substantially interfere with the pressure waves of the vibrating vibratable member or membrane which may result in loss of quality factor.

Figure 9:
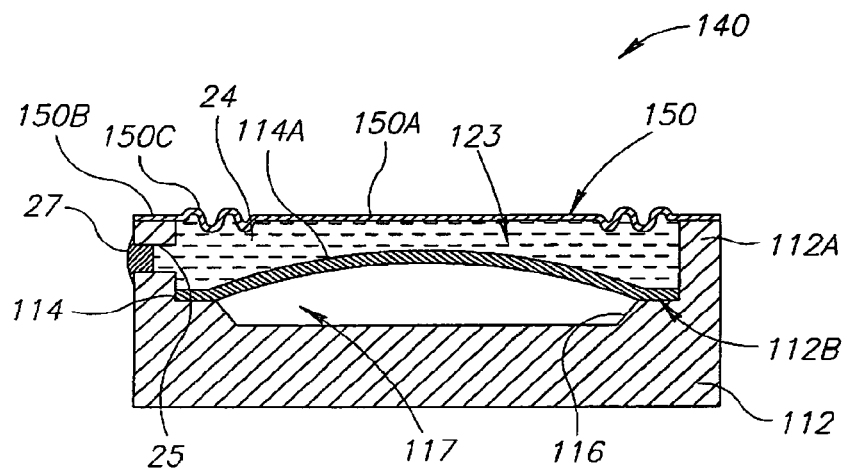
FIG. 9 is a schematic cross-sectional diagram illustrating a protected pressure sensor including a mechanically compliant member having a corrugated portion, in accordance with an embodiment of the present invention.

Reference is now made to FIG. 9 which is a schematic cross-sectional diagram illustrating a protected pressure sensor including a compliant member having a corrugated portion, in accordance with an embodiment of the present invention; and The pressure sensor 140 of FIG. 9 is similar but not identical to the pressure sensor 110 of FIG. 6. The substrate 112, the ridge 112A, the opening(s) 25, the sealing material 27, the second layer 114, the surface 112B, the surface 114A, and the substantially non-compressible medium 24 may be constructed as described in FIG. 6. However, while the sensor 110 of FIG. 6 has a compliant member 120 sealingly attached to the ridge 112A, to form the sealed chamber 122, the sensor 140 has a compliant member 150 sealingly attached to the ridge 112A to form a sealed chamber 123.

The compliant member 150 of FIG. 9 is different than the compliant member 120 of FIG. 6. The compliant member 150 of FIG. 9 is a mechanically compliant member including a first flat portion 150A, a second flat portion 150B and a corrugated portion 150C. The second flat portion 150B may be sealingly attached or glued to the ridge 112A of the substrate 112 to form a sealed chamber 123 which may be filled with the substantially non compressible medium 24 (such as, for example a substantially non-compressible liquid or gel) as disclosed in detail hereinabove for the sensor 110. Preferably, (but not obligatorily) the first flat portion 150A, the second flat portion 150B and the corrugated portion 150C are contiguous parts of the compliant member 150. The corrugated portion 150C allows the first portion 150A to move in order to communicate the pressure outside the sensor 140 to the medium 24 disposed within the chamber 123 and to the vibratable member 114A, and to communicate the pressure waves from the vibrating member (or vibrating membrane) to the outside medium disposed in the measurement environment.

Figure 10:
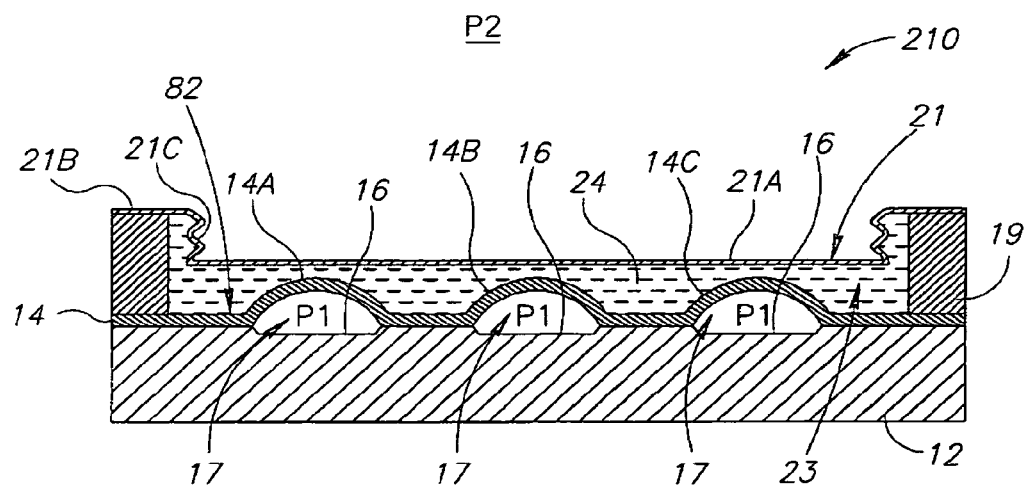
FIG. 10 is a schematic cross-sectional diagram illustrating a protected pressure sensor including a mechanically compliant member having a corrugated portion, in accordance with another embodiment of the present invention.

FIG. 10 is a schematic cross-sectional diagram illustrating a protected pressure sensor including a mechanically compliant member having a corrugated portion, in accordance with another embodiment of the present invention.

The sensor 210 of FIG. 10 is functionally similar but not structurally identical to the sensor 10 of FIG. 1. Like components of the sensors 10 and 210 are labeled with like reference numerals. The sensor 210 includes a compliant member 21. The compliant member 21 of FIG. 10 is different than the compliant member 20 of FIG. 1. The compliant member 21 of FIG. 10 is a mechanically compliant member including a first flat portion 21A, a second flat portion 21B and a corrugated portion 21C. The second flat portion 21B may be sealingly attached or glued to a spacer 19. The spacer 19 may be sealingly attached or glued to the substrate layer 12 (as disclosed in detail for the spacer 18 of FIG. 1 hereinabove) to form a sealed chamber 23 which may be filled with the substantially non compressible medium 24 (such as, for example a substantially non-compressible liquid or gel) as disclosed in detail hereinabove for the sensor 110. Preferably, (but not obligatorily) the first flat portion 21A, the second flat portion 21B and the corrugated portion 21C are contiguous parts of the compliant member 21. The corrugated portion 21C allows the first portion 21A to move in order to communicate the pressure outside the sensor 210 to the medium 24 disposed within the chamber 23 and to the vibratable membranes 14A, 14B and 14C of the sensor 210. The corrugated portion 21C also allows the pressure waves of the vibratable membranes 14A, 14B and 14C to be communicates to the medium in the measurement environment outside of the protected sensor.

The sensor 210 includes a spacer 19. The dimensions of the spacer 19 (of FIG. 10) may be different than the dimensions the spacer 18 (of FIG. 1) or may be identical to the dimensions of the spacer 18 (of FIG. 1), depending, inter alia, on the chosen dimensions of the compliant member 21.

It is also noted that the various parts and components of the drawing Figures (FIGS. 1-10) are not drawn to scale and the dimensions and shapes are drawn for illustrative purposes only (for the sake of clarity of illustration) and may not represent the actual dimensions of the various illustrated components. For example, the curvature of the vibratable membranes 14A, 14B and 14C of the second layer 14 (of FIG. 1) is greatly exaggerated (for illustrative purposes) relative to the actual curvature of the vibratable membranes of actual sensors.

It is further noted that while the particular examples of the sensors disclosed hereinabove and illustrated in FIGS. 1-10 are adapted for pressure measurements, the protected sensors of the present invention may be also used as temperature sensors as is known in the art and as disclosed hereinabove. It may generally be also possible to use the protected sensors of the present invention for determination of other physical parameters within a measurement environment, if the measured parameters influence the resonance frequency of the vibratable part(s) or vibratable membrane(s) of the sensor.

It is further noted that while the sensors disclosed hereinabove and illustrated in the drawing figures are implemented as sensors having a plurality of vibratable membranes (multi-membrane sensors), the protected sensors of the present invention may also be implemented as sensors having a single vibratable membrane or a single vibratable part such as, but not limited to, the sensors disclosed, inter alia, in U.S. Pat. Nos. 5,619,997, 5,989,190 and 6,083,165 to Kaplan, or any other sensors known in the art. All such sensors may be implemented as protected sensors by suitable use of a compliant member and a non-compressible medium to form a sealed chamber filled with the non-compressible medium in which the non-compressible medium transmits the physical variable to be measured to the vibratable part of the sensor or to a suitable coupler coupled to the vibratable part.

It will be appreciated by those skilled in the art, that the protected sensors of the present invention may be used for determining the value of a physical variable by using various different measurement methods. For example, the resonance frequency of the vibratable part(s) or the vibratable membrane(s) of the protected sensors disclosed hereinabove may be determined by using a continuous beam, or a pulsed beam, or a chirped beam of ultrasound for interrogating the protected sensors of the present invention and by measuring either the absorption of the energy of the exciting beam by the sensor, or the ultrasonic signal emitted by or returned from the sensor as is known in the art. Methods and systems for performing such measurement of the resonance frequency of passive sensors are disclosed in detail in U.S. Pat. Nos. 5,619, 997, 5,989,190 and 6,083,165, and 6,331,163 to Kaplan, and in co-pending U.S. patent application Ser. No. 10/828,218 to Girmonsky et al.

It is, however, noted that the method for protecting resonating sensors disclosed hereinabove is not limited for passive ultrasonic sensors disclosed hereinabove or to any particular measurement method disclosed hereinabove, but may be applied to any type of measurement method suitable for use with any type of resonating sensors, such as but not limited to, passive resonating sensors, active resonating sensors, optically interrogated active or passive resonating sensors, capacitive resonating sensors, or any other resonating sensor known in the art which has at least part of its resonating structure exposed to the measurement environment or medium, as long as they are interrogated by a sonic or ultrasonic beam.

It is further noted that during the construction of the protected sensors of the present invention (such as, for example, the sealed chamber 22 of the protected sensor 10) when the sealed chamber is filled with the medium 24 and sealed, care should be taken to avoid the trapping of any bubbles of gas or air in the sealed chamber. While it may still be possible to use a protected sensor containing such bubbles or gas filled spaces for performing measurements (depending, inter alia, on the size and cross-sectional area of such bubbles or gas filed spaces), such bubbles or any amount of gas or air trapped in the non-compressible medium 24 may undesirably affect or degrade the performance of the protected sensor because it introduces a compressible part (the gas in the space or a bubble containing a gas or gases) into the medium in the sealed chamber which may affect the actual pressure experienced by the vibratable membranes (such as, for example, the vibratable membranes 14A, 14B and 14C of the sensor unit 82) of the protected sensor, which may in turn introduce a certain measurement error. Additionally, gas bubbles trapped in the medium 24 contained within the sealed chamber may reflect or scatter part of the interrogating ultrasound beam, which may also undesirably affect the sensor's performance or the measurement system's performance.

Furthermore, the protected sensors of the present invention and parts thereof may be constructed of multilayered materials. For example, any of the recessed substrates, spacers, housings, and anchoring devices used in the construction of any of the protected sensors disclosed herein and illustrated in the drawings may (optionally) be formed as a multi-layered structure comprising more than one layer of material.

Moreover, if such multi-layered structures are used in a part of the protected sensor, some of the layers may or may not include the same materials.

Moreover, while the examples disclosed hereinabove may use certain exemplary gel types for implementing the protected sensors of the invention, many other types of gels may also be used. For example, other types of gels may be used in implementing the protected sensors of the present invention, such as, but not limited to, polyvinyl alcohol (PVAL) based gels, polyvinylpyrrolidone (PVP) based gels, polyethylene oxide (PEO) based gels, polyvinylmethyl ester (PVME) based gels, polyacrylamide (PAAM) based gels, or any other type of suitable gel or hydrogel or lipogel, or hydrophobic gel, or hydrophilic gel, known in the art.

It is noted that when the selected gel forming method includes the polymerization of a mixture containing suitable gel forming monomers (with or without cross-linking agents), the polymerization may be induced by any suitable method known in the art. For example one possible method of forming a gel is adding a polymerization initiating agent to a solution containing a monomer and (optionally a cross-linking agent). The polymerization initiating agent may be a suitable free-radical forming agent, such as, but not limited to, potassium persulphate in the case of using polyacrylamide forming monomers, or any other suitable polymerization initiating compound known in the art). However, It may also be possible to use other methods for initiating a polymerization of a monomer (or a mixture of different monomers) such as irradiating a suitable monomer(s) solution (with or without suitable cross-linking agents or other copolymers) with light having a suitable wavelength (such as, but not limited ultraviolet light, or light having other suitable wavelengths, or by using other types of ionizing radiation or other types of radiation. However, any other suitable method for initiating polymerization known in the art may be used in forming the gels included in the protected sensors of the present invention. It is further noted that many other types of gels and gel forming methods may be used in the present invention, as is known in the art. Such gels may include but are not limited to, agarose, alginates, gelatin, various polysaccharide based gels, protein based gels, synthetic polymer based gels (including cross-linked and non-cross-linked polymer based gels), and the like.

It is further noted that the protected sensors of the present invention and parts thereof may be constructed of multilayered materials. For example any of the recessed substrates, spacers, housings, and anchoring devices used in the construction of any of the protected sensors disclosed herein and illustrated in the drawings may (optionally) be a multi-layered structure comprising more than one layer of material.

Furthermore, if such multi-layered structures are used in a part of the protected sensor, some of the layers may or may not include the same materials.

Furthermore, it is noted that the vibratable members (or resonating members) of the sensor units used in the protected sensors of the present invention may have many different shapes and/or geometries. For example, the vibratable membranes of the passive ultrasonic sensor units disclosed hereinabove (such as, but not limited to, the vibratable membranes of the sensors 10, 30, 50, 80, 100, 110, 130, 140, 180 and 210) may have a circular shape, a rectangular shape, a polygonal shape, or any other shape known in the art and suitable for a vibratable resonator, as is known in the art. For example, the sensor illustrated in FIG. 2 of co-pending U.S. patent application Ser. No. 10/828,218 to Girmonsky et al., has multiple vibratable membranes having a rectangular shape, but other membrane shapes may be used.

It is further noted that, while all the embodiments of the protected sensor of the present invention are described and illustrated as having a single contiguous compliant member, in accordance with another embodiment of the present invention the sensors may be modified to include two or more separate compliant members suitably and sealingly attached to the sensor unit(s) or to the housing of the protected sensor(s) or to the anchor or support to which the sensor unit(s) are attached.

It will be appreciated by those skilled in the art that the methods disclosed hereinabove for protecting a sensor and for constructing protected sensors are not limited to the various exemplary embodiments disclosed and illustrated herein, and may be applied to other different sensors having vibratable parts or vibratable members. For example, the methods disclosed hereinabove may be applied to the passive ultrasonic sensors described in U.S. Pat. Nos. 5,989,190 and 6,083,165 to Kaplan, to construct protected passive ultrasonic sensors that are considered to be within the scope and spirit of the present invention. Thus, the vibratable member(s) or vibratable membrane(s) of the sensor unit(s) used for constructing the protected sensors of the present invention may be formed as a thin integral part of a recessed layer (such as, for example, the membrane 91 of the sensor 90 of FIG. 7 of U.S. Pat. No. 5,989,190 referenced above). Thus, the method disclosed herein of constructing protected sensors using resonating sensor unit(s), the substantially non-compressible medium and a compliant member, is a general method and may be generally applied to other suitable passive and active resonating sensors known in the art.

It is noted that while all the protected sensors disclosed hereinabove and illustrated in the drawings include one or more passive resonating sensor units, the protected sensors of the present invention are not limited to resonating sensor units only and may include additional types of sensor units. Thus, the protected sensors of the present invention may also include any other suitable type of sensor units known in the art. For example, in accordance with an embodiment of the present invention the protected sensor may include one or more resonating pressure sensor units as disclosed hereinabove and an additional non-resonating temperature sensor unit (not shown) of any suitable type known in the art. Such a temperature sensor unit may or may not be disposed within the chamber of the protected sensor. For example, if such a non resonating temperature sensor is included in a protected sensor of the type shown in FIG. 3, the additional temperature sensor unit may be disposed within the medium 24 in the sealed chamber 52, or alternatively may be suitably attached to the housing 54 such that it is disposed outside of the sealed chamber 52. Such non-resonating temperature sensor unit(s) (or any other type of non-resonating sensor unit(s) for measuring other physical or chemical parameters) may also be embedded in, or formed within, or included in, or suitably attached to the housing 54.

Many other types of combinations of resonating sensor units and non-resonating sensor units may be thus implemented in the protected sensors of the present invention as may be appreciated by the person skilled in the art. The non-resonating sensor units of such combinations of sensor units may be configured to determine any desired physical or chemical parameter in the measurement environment, as is known in the art. Thus, protected sensors including such combinations of resonating and/or non-resonating sensor units are included within the scope and spirit of the present invention.

It is noted that in embodiments in which the protected sensors of the present invention are configured to be disposed in contact with blood (such as, but not limited to protected pressure sensors which are designed to be implanted in a blood vessel or in any other part of the cardiovascular system), the parts of the sensor which come into contact with blood are preferably made from hemocompatible materials or suitably coated with hemocompatible materials, as is known in the art. The use of hemocompatible materials may be advantageous by, inter alia, reducing or preventing blood clotting, blood cells deposition, or other adverse effects.

It is further noted that while the chambers 22 (FIG. 1), 32 (FIG. 2), 52 (FIG. 3), 90 (FIG. 4), 90A-90C (FIG. 5), 122 (FIG. 6), 142A and 142 (FIG. 7), 102 (FIG. 8), 123 (FIG. 9) and 23 (FIG. 10) are illustrated as sealed chambers, this is not obligatory. Thus, when the medium 24 filling the chambers 22, 32, 52, 90, 90A, 90B, 90C, 122, 142A, 142, 102, 123, and 23 is a gel, the chambers 22, 32, 52, 90, 90A, 90B, 90C, 122, 142A, 142, 102, 123 and 23 may be open chambers (not shown in FIGS. 1-10), and need not obligatorily be completely sealed.

For example, if the compliant member 20 of the sensor 10 is glued or attached to the spacer 18 after casting a gel 24 into the sensor, the compliant member 20 need not fully and completely seal the formed chamber 22, because the sensor's performance does not substantially depend on the chamber 22 being a sealed chamber. Thus, the compliant member 20 may be non-sealingly attached to the spacer 18.

In another example, when the chamber 122 of the sensor 110 of FIG. 6 is filled with a gel through the opening 25 (as disclosed in detail hereinabove), the opening 25 may be left open (by not closing it with the sealing material 27 as described hereinabove with respect to FIG. 6). After gelling is completed, the solidified gel will stay in the chamber 122 even though the opening 25 stays open. Alternatively, when a gel is used within the chamber 122, the chamber 122 may also be sealed by closing the opening 25 with the sealing material 27 as disclosed in detail hereinabove for a liquid filled chamber.

Similarly, when using a gel as the medium 24, one or more suitable openings (not shown) may be made in any suitable parts of the other sensors illustrated above and such openings may be left open without substantially affecting the sensor's operation as a resonator. Such openings may be made in any suitable part of the sensor, including but not limited to, in the substrate layer 12 and/or in the layer 14 and/or in the spacer 18 and/or the compliant member 20 (of FIGS. 1 and 2), in the housing 34 and/or the compliant member 20A (FIG. 2), in the housing 54 and/or in the substrate layers 62 and/or 72, and/or in the layers 64 and/or 74 and/or the compliant member 54B (FIG. 3), in the substrate layer 82 and/or in the layer 14, and/or the anchor 88 and/or the compliant member 87 (of FIG. 4), in the in the substrate 82 and/or in the layer 14, and/or the anchor 89 and/or the compliant member 87 (of FIG. 5), in the substrate layer 112 and/or the layer 114 and/or the compliant member 120 (of FIG. 6), in the substrate 132 and/or the layer 144 and/or the spacer 138 and/or the compliant member 147 (of FIG. 7), in the sensor 5, and/or spacer 18 and/or the compliant member 20 (of FIG. 8), in the substrate 112 and/or the ridge 112A and/or the layer 114, and/or the compliant member 150 (of FIG. 9), in the substrate layer 12 and/or the layer 14 and/or the spacer 19 and/or the compliant member 21 (of FIG. 10).

However, since the particular examples of the sensors illustrated hereinabove are given by way of example only and many other sensor configurations are possible within the scope of the present invention, such an opening or openings may be formed in any other suitable part of the protected sensors of the present invention and/or between different parts of a sensor (such as, for example, by forming an opening between the spacer 18 and the substrate layer 12 of the sensor 10 by non-sealingly or incompletely attaching or gluing the spacer 18 to the substrate layer 12), depending, inter alia, on the resonating sensors' structure and configuration, the structure and configuration of the compliant member, and the presence and structure of spacer(s) or housing(s), anchors, or other sensor parts.

It is noted that while filling the sensors with the medium 24 through such openings (not shown) is possible (as disclosed in detail for the opening 25 of the sensor 110), this is not obligatory, and any other method for filling the sensors with the medium 24 (either a gel or a liquid) may be used as disclosed in detail hereinabove, or as is known in the art.

It is noted that in all of the protected sensors (with or without a compliant member) disclosed herein it is possible to coat or cover the entire surface of the protected sensor or a part of the sensor (such as, but not limited to, the housing of the sensor and/or the non-vibratable part(s) of a sensor unit or the compliant member of a protected sensor) with a thin compliant layer of material having special desired properties (the covering layer is not shown in the drawing figures for the sake of clarity of illustration). The addition of the covering layer may be done before, during or after the assembling or construction of the sensor, as is appropriate for specific sensor types. When such a covering layer is added on the compliant member the material of the layer should be sufficiently compliant and the covering layer may, preferably, have an acoustic impedance which is close to or equal to the acoustic impedance of the compliant member and/or the medium in the measurement environment.

The covering layer should be sufficiently compliant so as not to impair the sensor's performance. The covering layer may include one or more materials that may have a desired property, or may confer a desired property to any part of the sensor unit or of the protected sensor or may achieve a desirable effect. For example, the covering layer may include one or more hydrophilic materials or hydrophobic materials to confer desired hydrophilicity or hydrophobicity properties, respectively to the protected sensor or a part thereof. Furthermore, the covering layer may include one or more materials that may have desired hydrodynamic surface properties such as but not limited to the resistance (or friction coefficient) to flow of a fluid or liquid in contact with the surface of the coating layer.

Additionally, the covering layer may include one or more materials that may have one or more desired biological properties. For example, such material(s) may affect the growth of biological tissues or cells, as is known in the art. Biological effects may include but are not limited to, induction or inhibition of neointimal cell growth (or neointimal cell monolayer growth), affecting blood clot formation, inhibiting or promoting blood cell deposition and/or adhesion, or any other desirable biological effect(s) known in the art.

Alternatively or additionally, the present invention also includes modifying the surface properties of the compliant member(s) of the protected sensor, or of any other surface of any other part of the protected sensor (such as, but not limited to, the housing of the sensor, or a sensor anchor, or a spacer, or the like), using any suitable surface treatment or surface modification method known in the art, useful for changing the surface properties of the protected sensor or a part thereof. Such methods may include any chemical methods and/or physical methods for modifying a surface, as is known in the art. Foe example the protected sensor or any part(s) thereof may be treated chemically to change their surface properties, including but not limited to chemical surface properties, surface hydrophobicity, surface hydrophilicity, rheological surface properties, biological surface properties, surface resistance to deposition of cells or tissues thereon, or the like. The chemical treatment may be achieved by either chemically modifying surface chemical groups of the surface as is known in the art (such as, for example sillanization of surface hydroxyl groups), or by suitably attaching various different chemical molecules or moieties or biological molecules to the surface (with or without using linking molecules or agents). Such molecules or agents may include, but are not limited to, proteins, peptides, drugs, polysaccharides, lipids, glycolipids, lipoproteins, glycoproteins, proteoglycans, extracellular matrix components, nucleic acids, polynucleotides, RNA, DNA, anti-sense nucleic acid sequences, receptors, enzymes, antibodies, antigens, enzyme inhibitors, cell proliferation inhibitors, growth regulating factors, growth inhibiting factors, growth promoting factors, anti-coagulant agents, anti-clotting agents, tumor inhibiting drugs, tumor inhibiting factors, tumor suppressing agents, anti-cancer drugs, or any other type of molecule or factor or drug or agent having a desired biological or therapeutic property or effect, as is known in the art. Any suitable method known in the art may be used for performing such surface derivatization or surface modification or surface treatment, or surface attachment of agents or molecules, to any desired surface of the protected sensors of the present invention. Such methods for treating and/or modifying surfaces are well known in the art and will therefore not be discussed in details hereinafter.

While the invention has been described with respect to a limited number of embodiments, it will be appreciated that many variations, permutations and modifications may be made to the structure, dimensions, material composition, and construction methods of the protected sensors of the present invention, and other numerous applications of the protected sensors of the present invention which are all considered to be within the scope and spirit of the present invention.

What is claimed is:

1. A method for protecting an implantable, passive ultrasonically excitable resonating sensor from deposition of extraneous materials thereupon, the method comprising:
    providing a sensor having a passive ultrasonically excitable resonating sensor unit, said sensor unit including a substrate and a vibratable member, and a recess disposed between said vibratable member and said substrate to define a first chamber, said first chamber being a sensor unit chamber, said vibratable member having a resonance frequency that varies as a function of a physical variable in a measurement environment in which said sensor is disposed in response to an interrogating ultrasound beam; and forming a second chamber having walls to protect said vibratable member from the deposition of extraneous material thereupon, said second chamber defined between said vibratable member and a compliant member and filled with a substantially non-compressible medium, said compliant member having a first side and a second side and forming at least part of the walls of said second chamber, said vibratable member forming at least part of the walls of said second chamber;

wherein said substantially non-compressible medium is in contact with said compliant member and said vibratable member; wherein said first side of said compliant member is in contact with a measurement environment to form a first interface when said sensor is disposed in said measurement environment and said second side of said compliant member is in contact with said substantially non-compressible medium to form a second interface; and wherein said compliant member comprises a structure that limits reflection of said interrogating ultrasound beam at said first interface and said second interface, said structure selected from the group consisting of a material, a thickness, and a material and thickness.

2. The method according to claim 1, wherein said compliant member comprises a compliant material selected from a polymer based material, a plastic material, Kapton®, a polyurethane based polymer, an ethylvinyl acetate based polymer, Echothane® CPC-41, Echothane® CPC-29, Echothane®, and a Parylene® based polymer.

3. The method according to claim 1, wherein said forming step comprises sealingly enclosing said vibratable member of said resonating sensor unit in said second chamber to form a sealed second chamber.

4. The method according to claim 1, wherein said substantially non-compressible medium is selected from water, a water based solution, a liquid comprising one or more silicon based compounds and a gel, Dow Corning 710® Silicon Fluid, Fluorinert FC40 fluid, Fluorinert FC 70 fluid, a liquid having a low vapor pressure, and combinations thereof.

5. The method according to claim 1, wherein the acoustic impedance of said substantially non-compressible medium is close to or equal to the acoustic impedance of a medium contained in said measurement environment in which said protected sensor is disposed.

6. The method according to claim 1, wherein the acoustic impedance of said compliant member is close to or equal to the acoustic impedance of a medium contained in said measurement environment in which said protected sensor is disposed.

7. The method according to claim 1, wherein said resonating sensor unit is selected from a pressure sensor unit, a temperature sensor unit, a sensor for sensing the concentration of a chemical species in a measurement environment, and combinations thereof.

8. The method according to claim 1, wherein said forming step includes:
disposing said resonating sensor unit in a housing, filling said housing with said substantially non-compressible medium, and attaching said compliant member to said housing to form said second chamber.

9. The method according to claim 8, wherein said attaching comprises sealingly attaching said compliant member to said housing to form said second chamber.

10. The method according to claim 8, wherein said step of disposing comprises attaching said resonating sensor unit to said housing.

11. The method according to claim 1, wherein said forming step includes:
disposing said resonating sensor unit in a housing, attaching said compliant member to said housing to form said second chamber, and filling said second chamber with said substantially non-compressible medium.

12. The method according to claim 11, wherein said forming step further includes sealing said second chamber to form a sealed second chamber.

13. The method according to claim 11, wherein said step of disposing comprises attaching said resonating sensor unit to said housing.

14. The method according to claim 11, wherein a part of said housing forms at least part of the walls of said second chamber, and said filling includes introducing said substantially non-compressible medium into said second chamber through an opening formed in said part of said housing.

15. The method according to claim 1, wherein said second chamber is selected from
a second chamber formed within a sensor anchoring device, and
a second chamber comprising part of a sensor anchoring device.

16. The method according to claim 15, wherein said sensor anchoring device is selected from a sensor anchor, a sensor positioner, an implantable graft, a sensor fixating device, an implant, an implantable device, an implantable graft, a part of an implantable device, a pacemaker, part of a pacemaker, a defibrillator, part of a defibrillator, an implantable electrode, an insertable electrode, an endoscopic device, part of an endoscopic device, an autonomous endoscopic device, a part of an autonomous endoscopic device, a tethered endoscopic device, a part of a tethered endoscopic device, an implantable catheter, an insertable catheter, a stent, a part of a stent, a guide-wire, a part of a guide-wire, an implantable therapeutic substance releasing device, and an insertable therapeutic substance releasing device.

17. The method according to claim 1, wherein said forming step includes:
affixing a spacer member to said resonating sensor unit,
attaching said compliant member to said spacer member to form said second chamber, and
filling said second chamber with said substantially non-compressible medium.

18. The method according to claim 17, wherein said attaching is performed before said filling, and wherein said forming step further includes sealing said second chamber after said filling to form a sealed second chamber.

19. The method according to claim 17, wherein said attaching is performed after said filling.

20. The method according to claim 19, wherein said attaching comprises sealingly attaching said compliant member to said spacer member to form a sealed second chamber.

21. The method according to claim 19, wherein said attaching includes forming in situ said compliant member on said spacer member and on said substantially non-compressible medium to form said second chamber.

22. The method according to claim 19, wherein said in situ forming comprises depositing said compliant member on said spacer member and on said substantially non-compressible medium using a chemical vapor deposition method to form said second chamber.

23. The method according to claim 21, wherein said in situ forming comprises sealingly forming said compliant member on said spacer member and on said substantially non-compressible medium to form said sealed second chamber.

24. The method according to claim 17, wherein said attaching comprises sealingly producing in-situ said compliant member on said spacer member and on said substantially non-compressible medium using a chemical vapor deposition method to form said sealed second chamber.

25. The method according to claim 17, wherein said spacer member forms at least part of said walls of said second chamber and said filling is performed after said attaching, and wherein said filling includes introducing said substantially non-compressible medium into said second chamber through an opening in said spacer member.

26. The method according to claim 25, wherein said forming step further includes sealing said opening after said filling.

27. The method according to claim 25, wherein said introducing includes:
creating a vacuum within said second chamber,
disposing said sensor in a liquid to cover said opening with said liquid, and
allowing said liquid to fill said second chamber to produce said substantially non-compressible medium.

28. The method according to claim 27, wherein said liquid is a gel-forming liquid, said forming step further including allowing said gel-forming liquid to form a gel in said second chamber.

29. The method according to claim 28, wherein said gel-forming liquid is selected from: a liquefied form of said gel capable of gelling to form said gel, and a liquid gel precursor comprising reactants capable of reacting to form said gel.

30. The method according to claim 1, further including the step of applying a covering layer on at least part of said protected sensor to modify the surface properties of at least part of the surface of said protected sensor.

31. The method according to claim 30, wherein said covering layer is applied to said compliant member to change the surface properties thereof.

32. The method of claim 30, wherein said surface properties are selected from physical surface properties, chemical surface properties, electrochemical surface properties, biological surface properties, rheological surface properties, surface resistance to deposition of cells or tissues thereon, and any combinations thereof.

33. The method according to claim 1, further including the step of treating at least part of the surface of said protected sensor for modifying the surface properties of said at least part of said protected sensor.

34. The method according to claim 33, wherein said step of treating is performed on said compliant member to change the surface properties thereof.

35. The method according to claim 33, wherein said surface properties are selected from physical surface properties, chemical surface properties, electrochemical surface properties, biological surface properties, rheological surface properties, surface resistance to deposition of cells or tissues thereon, and any combinations thereof.

36. The method according to claim 33, wherein said step of treating comprises chemically treating said at least part of the surface of said protected sensor for modifying the surface properties thereof.

37. The method according to claim 1, wherein said substantially non-compressible medium is a gel.

38. The method according to claim 37, wherein said gel is selected from the group consisting of a synthetic gel, a natural gel, a hydrogel, a lipogel, a hydrophobic gel, a hydrophilic gel, a biocompatible gel, a hemocompatible gel, a polymer based gel, a cross-linked polymer based gel and combinations thereof.

39. The method of claim 1, wherein said compliant member has an acoustic impedance that matches the acoustic impedance of said non-compressible medium.

40. The method of claim 1, wherein said compliant member has an acoustic impedance in the range of 1.5-1.54 MRayls.

41. The method according to claim 1, wherein said forming step includes:
filling said second chamber with said substantially non-compressible medium, and attaching said compliant member to said sensor to form said second chamber.

42. The method according to claim 41, wherein said filling is performed after said attaching, and said filling includes introducing said substantially non-compressible medium into said second chamber through an opening formed in said walls other than said at least one vibratable member of said at least one second chamber.

43. The method according to claim 42, wherein said substrate includes a ridge, said compliant member is attached to said ridge prior to said filling, and said opening is located in said ridge.

44. The method according to claim 42, wherein said second chamber comprises part of a sensor anchoring device, and said opening is located in a suitable part of said sensor anchoring device.

45. The method according to any one of claim 14, 42, 43 or 44, wherein said forming step further includes sealing said opening after said filling to form a sealed second chamber.

46. The method according to claim any one of claim 14, 42, 43 or 44, wherein said introducing includes:
creating a vacuum within said second chamber,
disposing said sensor in a liquid to cover said opening with said liquid, and
allowing said liquid to fill said second chamber to produce said substantially non-compressible medium.

47. The method according to claim 46, wherein said liquid is a gel-forming liquid and wherein the method further includes the step of allowing said gel-forming liquid to form a gel in said second chamber.

48. The method of claim 47, wherein said gel-forming liquid is selected from: a liquefied form of said gel capable of gelling to form said gel, and a liquid gel precursor comprising reactants capable of reacting to form said gel.

49. The method of claim 48, wherein said gel-forming liquid is a liquefied form of said gel which was liquefied by heating said gel, and wherein said gel is formed within said second chamber upon cooling of said gel-forming liquid.

* * * * *